US012721850B2

(12) United States Patent
Raffa et al.

(10) Patent No.: US 12,721,850 B2
(45) Date of Patent: Sep. 1, 2026

(54) LARGE-CONDUCTANCE POTASSIUM CHANNEL MODULATORS, COMPOSITIONS THEREOF, METHODS OF MANUFACTURING THEREOF, AND METHODS OF USE THEREOF

(71) Applicant: ENALARE THERAPEUTICS INC., Princeton, NJ (US)

(72) Inventors: Robert B. Raffa, Tuscon, AZ (US); Joseph V. Pergolizzi, Naples, FL (US)

(73) Assignee: ENALARE THERAPEUTICS INC.

( * ) Notice: Subject to any disclaimer, the term of this patent is extended or adjusted under 35 U.S.C. 154(b) by 393 days.

(21) Appl. No.: 18/289,288

(22) PCT Filed: May 4, 2022

(86) PCT No.: PCT/US2022/027637
§ 371 (c)(1),
(2) Date: Nov. 2, 2023

(87) PCT Pub. No.: WO2022/235771
PCT Pub. Date: Nov. 10, 2022

(65) Prior Publication Data

US 2024/0238303 A1 Jul. 18, 2024

Related U.S. Application Data

(60) Provisional application No. 63/183,717, filed on May 4, 2021.

(51) Int. Cl.
*A61K 31/53* (2006.01)
*A61K 31/519* (2006.01)
*A61K 31/5355* (2006.01)

(52) U.S. Cl.
CPC ............ *A61K 31/53* (2013.01); *A61K 31/519* (2013.01); *A61K 31/5355* (2013.01)

(58) Field of Classification Search
CPC .............................. A61K 31/53; A61K 31/519
See application file for complete search history.

(56) References Cited

U.S. PATENT DOCUMENTS 9,162,992 B2 * 10/2015 Mannion .............. C07D 413/04
9,351,972 B2 5/2016 Dax et al.
2004/0198724 A1 10/2004 McNaughton-Smith et al.
2005/0043293 A1 2/2005 Gribkoff et al.
2005/0112128 A1 5/2005 Mckinsey et al.
2009/0111868 A1 4/2009 Marx et al.
2010/0256151 A1 10/2010 Ohmori et al.
2010/0256152 A1 10/2010 Takahashi
2014/0371224 A1 12/2014 Mannion et al.
2014/0378369 A1 12/2014 Barnett et al.
2019/0076528 A1 3/2019 Soden et al.
2020/0054558 A1 2/2020 Boucher et al.

FOREIGN PATENT DOCUMENTS

CN 108276410 A 7/2018
WO 2012074999 A1 6/2012
WO 2012092880 A1 7/2012
WO 2013181217 A2 12/2013
WO 2014078575 A2 5/2014
WO 2018007331 A1 1/2018
WO 2018011164 A1 1/2018

OTHER PUBLICATIONS

Tao et al. Long-term hypoxia increases calcium affinity of BK channels in ovine fetal and adult cerebral artery smooth muscle, Am J Physiol Heart Circ Physiol, Jan. 2015, pp. H707-H722 (Year: 2015).*

Extended European Search Report for European Application No. 22799485.2 mailed Feb. 26, 2025, 10 Pages.

Hawkinson J., et al., "Potent Pyrimidine and Pyrrolopyrimidine Inhibitors of Testis-Specific Serine/Threonine Kinase 2 (TSSK2)," ChemMedChem Communications, Oct. 2017, vol. 12(22), XP055708080, 15 Pages.

Roozekrans M., et al., "Two Studies on Reversal of Opioid-induced Respiratory Depression by Bk-channel Blocker GAL021 in Human Volunteers," The American society of Anesthesiologists, Sep. 2014, vol. 121(3), XP093169150, pp. 459-468.

Wang F., et al., "Molecular description of pyrimidine-based inhibitors with activity against FAK combining 3D-QSAR Analysis, molecular docking and molecular dynamics," Arabian Journal of Chemistry, Apr. 2021, vol. 14(6), XP086579870, pp. 1-17.

International Search Report of International Application No. PCT/EP2022/027637 mailed Sep. 16, 2022, 14 pgs.

* cited by examiner

*Primary Examiner* — Sarah Pihonak
*Assistant Examiner* — Mikhail O'Donnel Robinson
(74) *Attorney, Agent, or Firm* — Lowenstein Sandler LLP

(57) ABSTRACT

Disclosed herein are methods of treating a disease or condition modulated by large-conductance potassium channels, the methods including administering, to a patient in need thereof, an effective amount of a large-conductance potassium channel modulating compound. Exemplary disease or conditions that may be treated include, without limitations, protection against ischemia and hypoxia at multiple points throughout the body, as well as respiration stimulation in the presence of such conditions (both local and systemic). Also described herein are pharmaceutical compositions for use in the methods of treatment of a disease or condition modulated by large-conductance potassium channels, and methods of preparing such pharmaceutical compositions.

21 Claims, 1 Drawing Sheet

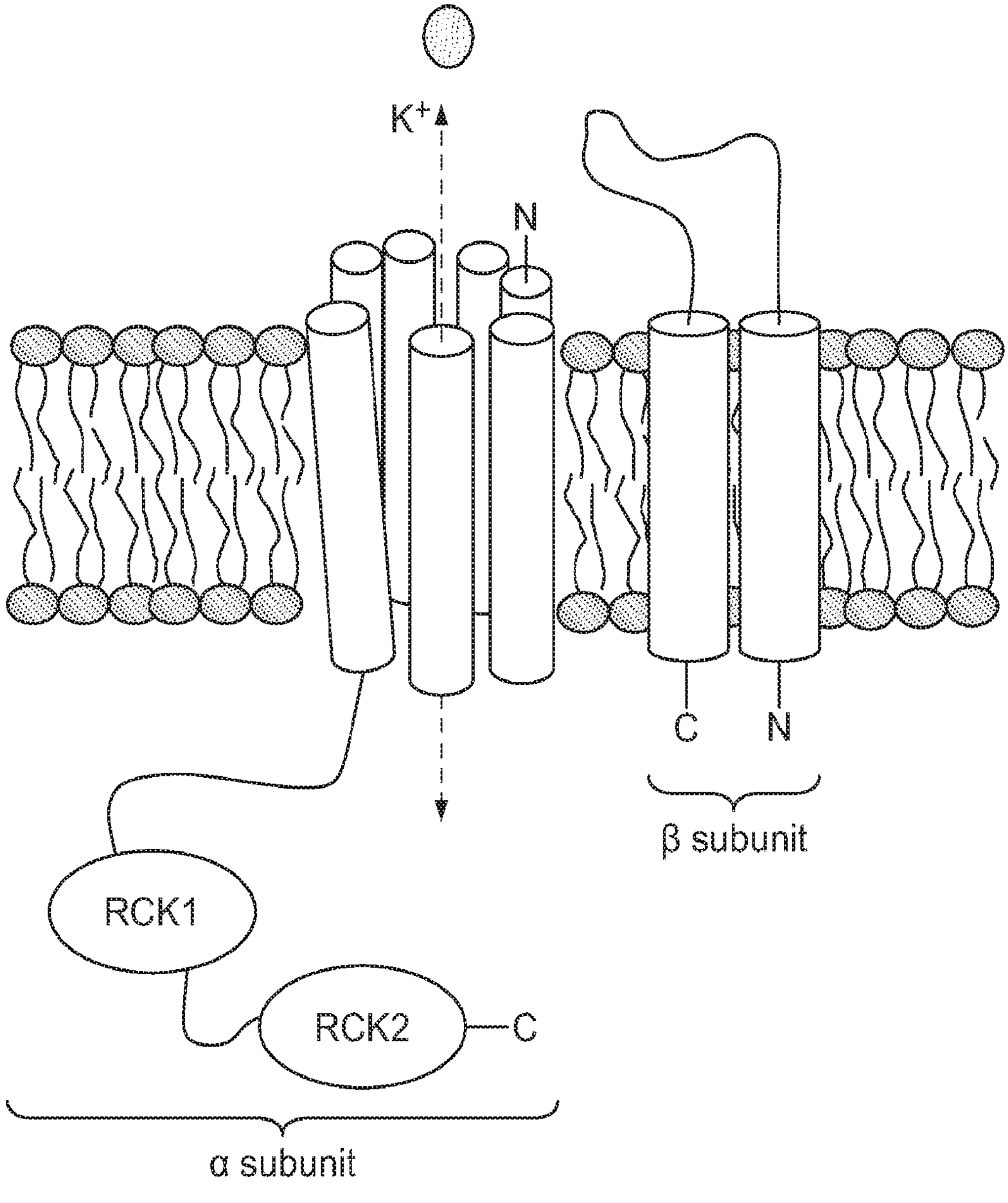
K+
N
C
N
β subunit
RCK1
RCK2
C
α subunit

LARGE-CONDUCTANCE POTASSIUM CHANNEL MODULATORS, COMPOSITIONS THEREOF, METHODS OF MANUFACTURING THEREOF, AND METHODS OF USE THEREOF

FIELD OF THE DISCLOSURE

The present disclosure relates to large-conductance potassium channel modulators, compositions thereof, methods of manufacturing thereof, and methods of use thereof in a treatment of a disease or a condition modulated by large-conductance potassium channels.

BACKGROUND OF THE DISCLOSURE

G-protein coupled receptors (GPCRs) are ubiquitous transmembrane receptor proteins that are major targets in disease-treatment and drug-development. They are currently the most common targets for FDA (United States Food and Drug Administration)-approved drugs. Although the GPCRs are more commonly focused upon, BK (big potassium) channels are perhaps even more fundamental. Due to variability in component composition and posttranslational modifications, BK channel subtypes are expressed in different frequencies in various organs/tissues, with differing chemo-sensitivities and 2nd-messenger transduction processes.

Although widely distributed, the physiological differences among BK channels which results from posttranslational modification (alternative splicing) and co-assembly with auxiliary modulatory subunits ($\beta_{1-4}$ and $\gamma_{1-4}$), bestows localized differences in subunit composition, distribution, $2^{nd}$-messenger coupling, and pharmacologic properties. Due to the ubiquitous nature of BK channels and the multiplicity of subtypes, they have many potential therapeutic applications in the maintenance of oxygen homeostasis, cerebro- and cardio-protection, and stimulation of respiration in response to drug-induced respiratory depression. BK channels may also offer other potentially broad and underrecognized promising targets for novel pharmaceutical development.

SUMMARY OF THE DISCLOSURE

In certain embodiments, the present disclosure is directed to a method of treating a disease or condition modulated by large-conductance potassium channels comprising administering, to a patient in need thereof, an effective amount of a large-conductance potassium channel modulating compound.

In certain embodiments, the present disclosure is directed to a method of treating a disease or condition modulated by large-conductance potassium channels comprising administering, to a patient in need thereof, an effective amount of a large-conductance potassium channel modulating compound of Formula (I):

(I)

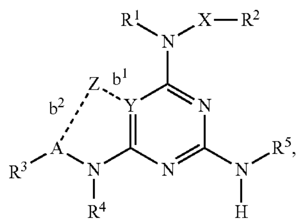

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

In certain embodiments, at least one substituent selected from the group consisting of $R^1$, $R^2$, $R^3$ and $R^5$, as described with respect to Formula (I) above, is alkynyl or substituted alkynyl.

In certain embodiments, the compound of Formula (I) is an agonist. In certain embodiments, the compound of Formula (I) is an antagonist. In certain embodiments, the compound of Formula (I) modulates at one or both of the pore gate or the voltage sensing domain of the large-conductance potassium channel. In certain embodiments, the compound of Formula (I) modulates at one or both of the RCK1 or the RCK2 of the large-conductance potassium channel.

In certain embodiments, the present disclosure is directed to a method for treating a disease or condition that is a neurological disorder. In certain embodiments, the neurological disorder is epilepsy, paroxysmal, dyskinesia, or schizophrenia.

In certain embodiments, the present disclosure is directed to a method for treating a disease or condition that is a cardiac disorder. In certain embodiments, the cardiac disorder is cardiac ischemia or cardiac hypoxia.

In certain embodiments, the present disclosure is directed to a method for treating a disease or condition that is a cerebral disorder. In certain embodiments, the cerebral disorder is cerebral ischemia or cerebral hypoxia.

In certain embodiments, the present disclosure is directed to a method for treating a disease or condition that requires organ protection. In certain embodiments, the organ protection is one or both of cerebro and cardio.

In certain embodiments, the large-conductance potassium channel, modulated by the compound of Formula (I), is located at one or both of a pre-synaptic or post-synaptic site. In certain embodiments, the large-conductance potassium channel, modulated by the compound of Formula (I), is located at one or both of cardiovascular smooth muscle and cardiac fibroblasts. In certain embodiments, the large-conductance potassium channel, modulated by the compound of Formula (I), is located at one or both of airway surface liquid and mucociliary clearance.

In certain embodiments, the compound of Formula (I) is administered via a route that is selected from oral, intravenous, nasal, inhalational, topical, buccal, rectal, pleural, peritoneal, vaginal, intramuscular, subcutaneous, transdermal, epidural, intratrachael, otic, intraocular, or intrathecal route.

In certain embodiments, the present disclosure is directed to a pharmaceutical composition comprising an effective amount of a large-conductance potassium channel modulating compound of Formula (I):

(I)

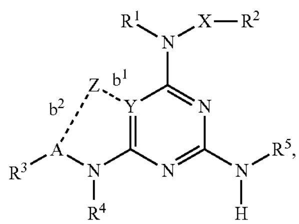

wherein:

- $R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;
- $R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;
- $R^4$ is H, alkyl, or substituted alkyl;
- $R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;
- $R^6$ is H, alkyl, substituted alkyl or alkenyl;
- X is a bond, O or $NR^4$; and,
- Y is N, $CR^6$ or C; wherein:
  - if Y is N or $CR^6$, then bond $b^1$ is nil and: (i) Z is H, bond $b^2$ is a single bond, and A is CH; or, (ii) Z is nil, bond $b^2$ is nil, and A is a single bond; and,
  - if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof, and a pharmaceutically acceptable excipient.

In certain embodiments, the present disclosure is directed to a pharmaceutical composition comprising an effective amount of a large-conductance potassium channel modulating compound of Formula (I), as described above, where at least one substituent selected from the group consisting of $R^1$, $R^2$, $R^3$ and $R^5$ is alkynyl or substituted alkynyl.

In certain embodiments, the present disclosure is directed to a method of preparing any of the pharmaceutical compositions described herein.

BRIEF DESCRIPTION OF THE DRAWINGS

The above and other features of the present invention, their nature, and various advantages will become more apparent upon consideration of the following detailed description, taken in conjunction with the accompanying drawings, in which:

FIG. 1 provides a representations of a transmembrane BK channel, showing the pore-related α subunit with $Ca^{2+}$-sensing RCK1 and RCK2, and accessory β subunit. Variations in each of the components provides diversity in sensitivity and response.

DEFINITIONS

As used herein, the singular forms "a," "an," and "the" include plural references unless the context clearly indicates otherwise. Thus, for example, reference to "an active agent" includes a single active agent as well as a mixture of two or more different active agent, and reference to an "excipient" includes a single excipient as well as a mixture of two or more different excipients, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number±10%, such that "about 10" would include from 9 to 11.

As used herein, the terms "active agent," "active ingredient," and "active pharmaceutical ingredient" refer to any material that is intended to produce a therapeutic, prophylactic, or other intended effect, whether or not approved by a government agency for that purpose. These terms with respect to specific agents include all pharmaceutically active agents, all pharmaceutically acceptable salts thereof, complexes, stereoisomers, crystalline forms, co-crystals, ether, esters, hydrates, solvates, and mixtures thereof, where the form is pharmaceutically active.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

The term "patient" refers to a subject, an animal or a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are otherwise healthy.

"Pharmaceutically acceptable salts" or "salts" include, but are not limited to, inorganic acid salts such as hydrochloride, hydrobromide, hydroiodic, sulfate, hydrogen sulfate, phosphate, nitric, carbonic, sulfuric, phosphoric (including hydrogen phosphate and dihydrogen phosphate), and the like; organic acid salts such as an oxalate, a malonate, a citrate, a fumarate, a lactate, a malate, a succinate, formate, acetate, trifluoroacetate, maleate, tartrate, a gluconate, a benzoate, a salicylate, a xinafoate, a pamoate, an ascorbate, an adipate, a cinnamte, and the like; sulfonates such as methanesulfonate, benzenesulfonate, p-toluenesulfonate and the like; amino acid salts such as arginate, asparaginate, glutamate and the like; metal salts such as zinc salt, sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt, chloroprocaine, choline, diethanolamine, ethylenediamine, meglumine (N-methylglucamine) and procaine, and the like. These salts may be present in the form of a hydrate, a solvate, or a crystalline polymorph. In certain embodiments, appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. All of these salts may be prepared by conventional means from the corresponding compound of the invention by reacting, for example, the appropriate acid or base with the compound of the invention. *Handbook of Pharmaceutical Salts: Properties, and Use* (P. H. Stahl & C. G. Wermuth eds., Verlag Helvetica Chimica Acta, 2002) [1].

The term "disease" or "diseases" or "condition" or "conditions" refers to those medical conditions that can be treated or prevented by administration to a subject of an effective amount of an active agent.

The terms "treatment of" and "treating" includes the lessening of the severity of or cessation of a condition or lessening the severity of or cessation of symptoms of a condition. In certain embodiments, the terms "treatment" or "treating" with respect to a condition means administration with the intent to provide a pharmacodynamics effect, regardless of the outcome. In certain embodiments, "treatment" or "treating" means "having positive effect on a condition" and encompass reduction in the severity, amelioration, and/or alleviation of at least one symptom of a condition; a reduction, amelioration, and/or alleviation in the severity of the conditions; delay, prevention, or inhibition of the progression of the condition; or a perceived improvement or benefit as a result of the treatment. Treatment, as used herein, does not require total curing of the condition. In certain embodiments, a composition of the present disclosure may provide improvement to a patient's quality of life, or delay, prevent, inhibit the onset of one or more symptoms of a condition, or provide a perceived benefit.

The terms "prevention of" and "preventing" includes the avoidance of the onset of a condition.

The term "therapeutically effective amount" is intended to include an amount of an active agent, or an amount of the combination of active agents, e.g., to treat or prevent the condition, or to treat the symptoms of the condition, in a subject.

The term "effective amount" is intended to include an amount of a component, or an amount of a combination of component, to achieve a certain result or property, for instance, an effective amount of a pH adjusting agent to achieve a pH of 6.0 is intended to include an amount of one or more pH adjusting agents to arrive at a pH of 6.0.

The terms "application," "apply," and "applying" with respect to a disclosed topical composition, or method of using a disclosed topical composition, refer to any manner of administering a topical composition to the skin of a patient which, in medical or cosmetology practice, delivers the composition to the patient's skin surface. Smearing, rubbing, spreading, spraying a disclosed topical composition, with or without the aid of suitable devices, on a patient's skin are all included within the scope of the term "application," as used herein. The terms "topical" or "topically" with respect to administration or application of a disclosed formulation refer to epicutaneous administration or application, or administration onto skin.

As used herein, "oral delivery" or "oral administration" refers to a route of administration wherein the composition is taken through the mouth. Oral administration is a part of enteral administration, which also includes buccal (dissolved inside the cheek), sublabial (dissolved under the lip), and sublingual administration (dissolved under the tongue). In certain embodiments, oral administration includes a route of administration wherein the composition is ingested. In certain embodiments, oral administration includes a route of administration wherein the composition is inhaled.

As used herein, "parenteral administration" refers to a route of administration wherein the pharmaceutical dosage form is injected, e.g., to the muscle (intramuscular administration), to the vein (intravenous administration), under the skin (subcutaneous administration).

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

As used herein, the term "alkyl," by itself or as part of another substituent means, unless otherwise stated, a straight or branched chain hydrocarbon having the number of carbon atoms designated (i.e. C1-C10 means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is (C1-C6) alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e. C3-C6 means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is (C3-C6)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —CH2-CH═CH2.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —NH2, —N(CH3)2, (1-methyl-imidazol-2-yl), pyridin-2-yl, pyridin-3-yl, pyridin-4-yl, —C(═O)OH, trifluoromethyl, —C≡N, —C(═O)O(C1-C4)alkyl, —C(═O)NH2, —C(═O)NH(C1-C4)alkyl, —C(═O)N((C1-C4)alkyl)2, —SO2NH2, —C(═NH)NH2, and —NO2, preferably containing one or two substituents selected from halogen, —OH, alkoxy, —NH2, trifluoromethyl, —N(CH3)2, and —C(═O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C1-C3) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: $—O—CH_2—CH_2—CH_3$, $—CH_2—CH_2—CH_2—OH$, $—CH_2—CH_2—NH—CH_3$, $—CH_2—S—CH_2—CH_3$, and $—CH_2CH_2—S(═O)—CH_3$. Up to two heteroatoms may be consecutive, such as, for example, $—CH_2—NH—OCH_3$, or $—CH_2—CH_2—S—S—CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include $—CH═CHO—CH_3$, $—CH═CH—CH_2—OH$, $—CH_2—CH═N—OCH_3$, $—CH═CH—N(CH_3)—CH_3$, and $—CH_2—CH═CH—CH_2—SH$.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-$(C_1$-$C_3)$alkyl" means a functional group wherein a one to three carbon alkylene chain is attached to an aryl group, e.g., $—CH_2CH_2$-phenyl or $—CH_2$-phenyl (benzyl). Preferred is aryl-$CH_2—$ and aryl-$CH(CH_3)—$. The term "substituted aryl-$(C_1$-$C_3)$alkyl" means an aryl-$(C_1$-$C_3)$alkyl functional group in which the aryl group is substituted. Preferred is substituted aryl $(CH_2)—$. Similarly, the term "heteroaryl-$(C_1$-$C_3)$alkyl" means a functional group wherein a one to three carbon alkylene chain is attached to a heteroaryl group, e.g., $—CH_2CH_2$-pyridyl. Preferred is heteroaryl-$(CH_2)—$. The term "substituted heteroaryl-$(C_1$-$C_3)$alkyl" means a heteroaryl-$(C_1$-$C_3)$alkyl functional group in which the heteroaryl group is substituted. Preferred is substituted heteroaryl-$(CH_2)—$.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

DETAILED DESCRIPTION

Method of Treatment

There are three main subfamilies of $Ca^{2+}$-activated potassium channels, SK (small conductance), IK (intermediate conductance), and BK (big conductance). The terms "large-conductance potassium channels" and "BK channels" may be used interchangeably throughout this disclosure. The BK channels (encoded by the Kcnma1 gene) are also called $BK_{Ca}$, MaxiK, Slo1, KCa1.1, and KCNMA1, among other names. They were first cloned in 1992, and based on their modulatory roles have been described as the "universal regulator of cellular excitability" and even "king of ion channels". BK channels are voltage- and $Ca^{2+}$-sensitive potassium channels, tetramers formed of a subunits. BK a subunits differ from the SK/IK group in the existence of an additional transmembrane helix which drives the N-terminus to the extracellular side of the plasma membrane. Each membrane-spanning domain of a BK channel contains a pore-gate and voltage-sensing domain. These two domains are made of two regulators of conductance of potassium, RCK1 and RCK2. The RCK1-RCK2 link with BK channels is highly conserved.

BK channels allow rapid and large influxes of potassium through the channel, thus hyperpolarizing the membrane. Conformational change of the subunits and channels transduces and stabilizes the channel pore in its open state. The large ('big') influx is 10-20 times larger than most other $K^+$ channels. They can form homo- and hetero-multimeric channels and can be expressed on both pre and post synaptic sites. BK channels can detect intracellular calcium concentrations as well as membrane depolarization independently. This puts the BK channel in a "unique" position to control of excitable cells. And the expression of particular BK subunit subtypes tune the BK channels to the local signaling environment. The different subunit subtypes differentiate the functional expression of these channels. BK channel currents abruptly increase during the first two weeks after birth in animal models, which may be coincident with their functional maturation as the channels adjust (to) neuronal properties as the animal matures. This is an "experience dependent plasticity" that helps shape how BK channels will function in the mature animal.

For most ion channels, functional identity is defined by properties conferred by the pore-forming subunits of the channel. In contrast, an enormous diversity in BK channel function arises from a merging together with non-pore-forming regulatory subunits. The same BK pore-forming subunits can participate in channels that could be considered to be entirely functionally distinct, as a simple consequence of the "wardrobe" of regulatory subunits that can decorate the pore-forming subunits (FIG. 1). FIG. 1 provides a representation of a transmembrane BK channel, showing the pore-related a subunit with $Ca^{2+}$-sensing RCK1 and RCK2, and accessory 3 subunit. Variations in each of the components provides diversity in the sensitivity and the response of the BK channel.

It is believed, without being construed as limiting, that because of the extensive diversity of BK channels subtypes (subunit composition, 3-D arrangement, and accessory molecules), distribution, and pharmacology, BK channels could participate in the maintenance of protection against ischemia and hypoxia at multiple points throughout the body. For instance, it is believed that BK channels play a role in providing cerebro- and cardio-protective actions against ischemia and hypoxia, and stimulate respiration in the presence of such conditions (both local and systemic). The inventors of the instant disclosure believe, without being construed as limiting, that BK channels participate in a coordinated control system, that is, BK channels work in concert to provide protection against ischemia and hypoxia not only where it occurs, but also preventing and/or treating and/or ameliorating and/or minimizing negative consequences at distal sites.

Certain embodiments of the instant disclosure are directed to methods for treating a disease or a condition modulated by large-conductance potassium channels comprising administering, to a patient in need thereof, an effective amount of a large-conductance potassium channel modulating compound. In certain embodiments, the large-conductance potassium channel modulating compound is selected from compounds of Formula (I):

(I)

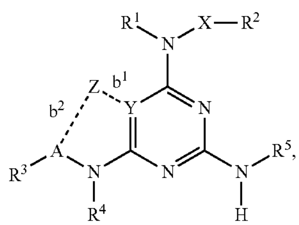

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

Certain embodiments of the instant disclosure are directed to methods for treating a disease or a condition modulated by large-conductance potassium channels comprising administering, to a patient in need thereof, an effective amount of a large-conductance potassium channel modulating compound selected from Formula (I):

(I)

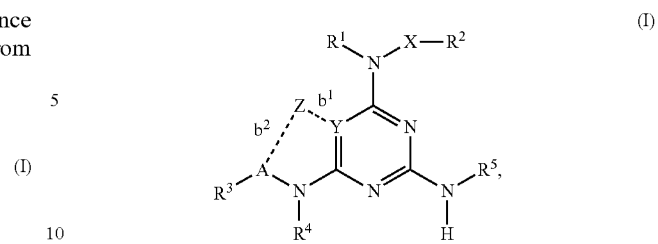

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl; wherein at least one substituent selected from the group consisting of $R^1$, $R^2$, $R^3$ and $R^5$ is alkynyl or substituted alkynyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

Certain embodiments of the instant disclosure are directed to methods for treating a disease or a condition modulated by large-conductance potassium channels comprising administering, to a patient in need thereof, an effective amount of a large-conductance potassium channel modulating compound selected from Formula (I):

(I)

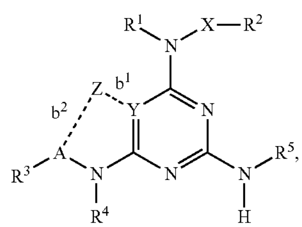

wherein:

$R^1$ and $R^2$ are independently H, alkyl, substituted alkyl, cycloalkyl, substituted cycloalkyl, alkenyl, substituted alkenyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

In one embodiment, $R^3$ is H, alkyl, substituted alkyl, cycloalkyl, substituted cycloalkyl, alkenyl, or substituted alkenyl. In another embodiment, $R^5$ is H, alkyl, substituted alkyl, cycloalkyl, substituted cycloalkyl, alkenyl, substituted alkenyl, or acyl.

Certain embodiments of the instant disclosure are directed to methods for treating a disease or a condition modulated by large-conductance potassium channels comprising administering, to a patient in need thereof, an effective amount of a large-conductance potassium channel modulating compound selected from Formula (I):

(I)

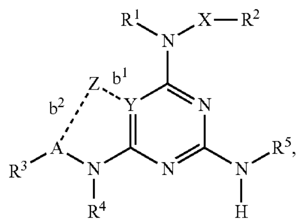

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl or substituted alkynyl;

$R^4$ is H, alkyl, or substituted alkyl;

$R^5$ is alkyl, propargylic, substituted propargylic, homopropargylic, or substituted homopropargylic, wherein at least one substituent selected from the group consisting of $R^1$, $R^2$, $R^3$ and $R^5$ is alkynyl or substituted alkynyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and:

(i) Z is H, bond $b^2$ is a single bond, and A is CH; or, (ii) Z is nil, bond $b^2$ is nil, and A is a single bond; and, if Y is C, then bond $b^1$ is a single bond, and:

(i) Z is $CH_2$, bond $b^2$ is a single bond, and A is CH; or, (ii) Z is CH, bond $b^2$ is a double bond, and A is C;

or a salt thereof.

In certain embodiments, (i) $R^3$ is H, alkyl or substituted alkyl, and $R^5$ is propargylic, substituted propargylic, homopropargylic, or substituted homopropargylic, or (ii) $R^3$ is H or alkynyl, and $R^5$ is alkyl, propargylic, substituted propargylic, homopropargylic, or substituted homopropargylic.

In one embodiment, the at least one compound of formula (I) is selected from the group consisting of (i) Y is N, bond b1 is nil, Z is H, bond b2 is a single bond, A is CH, and the at least one compound is a compound of formula (II-a) or a salt thereof:

(II-a)

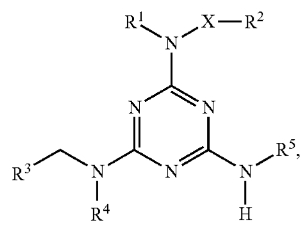

and (ii) Y is N, bond b1 is nil, Z is nil, bond b2 is nil, and A is a bond, and the compound of the invention is a compound of formula (II-b) or a salt thereof:

(II-b)

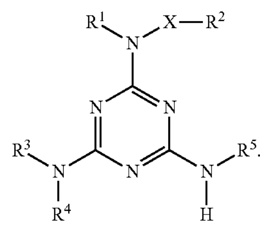

In one embodiment, the at least one compound of formula (I) is selected from the group consisting of: (i) Y is $CR^6$, bond $b^1$ is nil, Z is H, bond $b^2$ is a single bond, A is CH, and the at least one compound is a compound of formula (III-a) or a salt thereof:

(III-a)

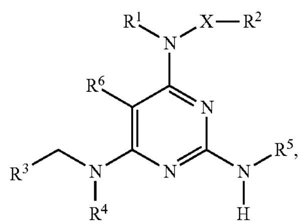

and (ii) Y is $CR^6$, bond $b^1$ is nil, Z is nil, bond $b^2$ is nil, and A is a bond, and the compound of the invention is a pyrimidine of formula (III-b) or a salt thereof:

(III-b)

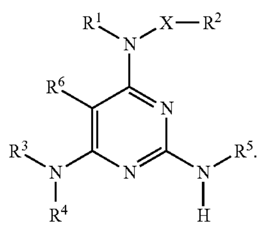

In one embodiment, Y is C, bond $b^1$ is a single bond, Z is $CH_2$, bond $b^2$ is a single bond, A is CH, and said at least one compound is a compound of formula (IV) or a salt thereof:

(IV)

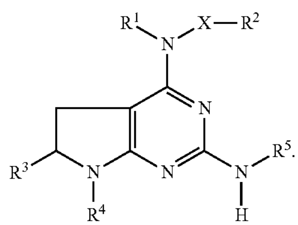

In one embodiment, Y is C, bond $b^1$ is a single bond, Z is CH, bond $b^2$ is a double bond, A is C, and said at least one compound is a compound of formula (V) or a salt thereof:

(V)

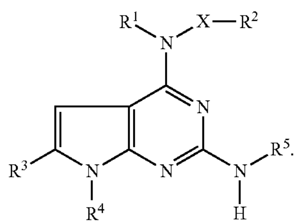

In one embodiment, the at least one compound is selected from the group consisting of: N-(4,6-Bis-methylamino-[1,3,5]triazin-2-yl)-N,O-dimethyl-hydroxylamine (XX), N-(4,6-Bis-ethylamino-[1,3,5]triazin-2-yl)-N,O-dimethyl-hydroxylamine (XXII), N-(4-Cyclopropylmethylamino)-N-(6-n-propylamino) [1,3,5]triazin-2-yl)-N,O-dimethyl-hydroxylamine (XXV), N-(4-Ethylamino)-N-(6-n-propylamino)-[1,3,5]triazin-2-yl)-N,O-dimethyl-hydroxylamine (XXVII), N-(Bis-4,6-(2-methylpropylamino)) [1,3,5]triazin-2-yl)-N,O-dimethyl-hydroxylamine (XXIX), N-(Bis-4,6-(2,2-dimethylpropylamino)) [1,3,5]triazin-2-yl)-O,N-dimethyl-hydroxylamine (XXXI), 4,6-Bis-N-cyclopropylamino-[1,3,5]triazin-2-yl)-N,O-dimethyl-hydroxylamine hydrochloride (XXXIII), N-(4,6-Bis-n-propylamino-[1,3,5]triazin-2-yl)-O,N-dimethyl-hydroxylamine (XXXV), N-(4-(Methoxy(methyl)amino)-6-(propylamino)-1,3,5-triazin-2-yl)propionamide (XL), N-(4,6-Bis-propylamino-[1,3,5]triazin-2-yl)-O-methyl-hydroxylamine (XLI), O-Allyl-N-(4,6-bis-propylamino-[1,3,5]triazin-2-yl)-hydroxylamine (XLIII), N-(4,6-Bis-propylamino-[1,3,5]triazin-2-yl)-hydroxylamine (XLV), 6-(Methoxy(methyl)amino)-N2-propyl-1,3,5-triazine-2,4-diamine (XLVII), N-(4,6-Bis-propylamino-[1,3,5]triazin-2-yl)-N-methyl-hydroxylamine (XLVIII), O-Benzyl-N-(4,6-bis-propylamino-[1,3,5]triazin-2-yl)-N-methyl-hydroxylamine (LIII), N-(4,6-Bis-propylamino-[1,3,5]triazin-2-yl)-N-isopropyl-hydroxylamine (LV), 6-[1,2]Oxazinan-2-yl-N,N'-dipropyl-[1,3,5]triazine-2,4-diamine (LVII), N-(4,6-Bis-propylamino-[1,3,5]triazin-2-yl)-O-isopropyl-N-methyl-hydroxylamine (LXIV), O-Benzyl-N-(4,6-bis-propylamino-[1,3,5]triazin-2-yl)-N-ethyl-hydroxylamine (LXVIII), N-(4,6-Bis-propylamino-[1,3,5]triazin-2-yl)-O-isopropyl-hydroxylamine (LXX), 6-((Benzyloxy)(isopropyl)amino)-N2,N4-dipropyl-1,3,5-triazine-2,4-diamine (LXXII), N-(4,6-Bis-propylamino-[1,3,5]triazin-2-yl)-N-ethyl-O-isopropyl-hydroxylamine (LXXVI), N-(4,6-Bis-propylamino-[1,3,5]triazin-2-yl)-O-isobutyl-N-methyl-hydroxylamine (LXXXII), 6-(Methyl(thiophen-2-ylmethoxy)amino)-N2,N4-dipropyl-1,3,5-triazine-2,4-diamine (LXXXIV), N-(4,6-Bis-propylamino-[1,3,5]triazin-2-yl)-O-cyclopropylmethyl-N-methyl-hydroxylamine (XCI), N-(4,6-Bis-propylamino-[1,3,5]triazin-2-yl)-O-ethyl-N-methyl-hydroxylamine (XCVI), N-(4,6-Bis-propylamino-[1,3,5]triazin-2-yl)-O-(2,2-difluoro-ethyl)-hydroxylamine (C), 4-N-(2-Dimethylaminoethyl)amino-6-N-(n-propyl)amino-[1,3,5]triazin-2-yl)-N,O-dimethyl-hydroxylamine (CIII), 4-N-(3-(1-N-Methylimidazol-2-yl)-propyl)-amino-6-N-(n-propyl)amino-[1,3,5]triazin-2-yl)-N,O-dimethyl-hydroxylamine (CV), 4-N-(1-N-Methylimidazol-2-yl)-methylamino-6-N-(n-propyl)amino-[1,3,5]triazin-2-yl)-O,N-dimethyl-hydroxylamine (CVII), 4,6-Bis-(N-(2-dimethylaminoethyl)amino)-[1,3,5]triazin-2-yl)-N,O-dimethyl-hydroxylamine (CIX), 4,6-Bis-(N-(pyridin-4-ylmethyl)amino)-[1,3,5]triazin-2-yl)-N,O-dimethyl-hydroxylamine (CXI), 4,6-Bis-[N-(3-methoxy-n-propyl)amino]-[1,3,5]triazin-2-yl)-N,O-dimethyl-hydroxylamine (CXIII), 4,6-Bis-[N-(tetrahydropyran-4-ylmethyl)amino]-[1,3,5]triazin-2-yl)-N,O-dimethyl-hydroxylamine (CXV), N-(5,8,11-Trioxa-2,14,16,18,19-pentaazabicyclo[13.3.1]-nonadeca-1(18),15(19),16(17)-trien-17-yl)-N,O-dimethyl-hydroxylamine (CXVII), N-(4,6-Bis-propylamino-[1,3,5]triazin-2-yl)-N',N'-dimethylhydrazine (XLVI), N-(4,6-Bis-propylamino-[1,3,5]triazin-2-yl)-N-methyl-N'-methylhydrazine (XLIX), a salt thereof and mixtures thereof. In another embodiment, the salt is hydrogen sulfate or hydrochloride.

In one embodiment, the at least one compound is 2,6-bis-(N-n-propylamino)-[1,3]pyrimidin-4-yl)-N,O-dimethyl-hydroxylamine N-(4-(Methoxy(methyl)amino)-6-(propylamino)-1,3,5-triazin-2-yl)propionamide or a salt thereof. In another embodiment, the salt is hydrogen sulfate or hydrochloride.

In one embodiment, the at least one compound is N-(4-(Methoxy(methyl)amino)-6-(propylamino)-1,3,5-triazin-2- yl)propionamide or a salt thereof. In another embodiment, the salt is hydrogen sulfate or hydrochloride.

In one embodiment, the at least one compound is selected from the group consisting of: 2-(n-Propyl)amino-4-(i-propylamino-7-methyl-pyrrolidino[2,3-d]pyrimidine (CXXVI), 2-(n-Propyl)amino-4-dimethylamino-7-methyl-pyrrolidino [2,3-d]pyrimidine (CXXVIII), 2-(n-Propyl)amino-4-methylamino-7-methyl-pyrrolidino[2,3-d]pyrimidine (CXXXI), 2-(n-Propyl)amino-4-(i-propyl)amino-7-i-propyl-pyrrolidino[2,3-d]pyrimidine (CXXXVI), 2,4-Bis-(n-propyl) amino-7H-pyrrolidino[2,3-d]pyrimidine (CXLIX), 2-(n-Propyl)amino-4-(4-hydroxypiperidin-1-yl)-7-methyl-pyrrolidino[2,3-d]pyrimidine (CLII), 8-(7-Methyl-2-(propylamino)-pyrrolidino[2,3-d]pyrimidin-4-yl)-8-azabicyclo[3.2.1]octan-3-ol (CLV), a salt thereof and mixtures thereof. In another embodiment, the salt is hydrogen sulfate or hydrochloride.

In one embodiment, the at least one compound is selected from the group consisting of: N-(2-Propylamino-7H-pyrrolo [2,3d]pyrimidin-4-yl)-O,N-dimethyl-hydroxylamine (CXLI), N-(2-(Propen-2-yl)amino-7-methyl-pyrrolo[2,3d] pyrimidin-4-yl)-N,O-dimethyl-hydroxylamine (CLVIII), N-(2-(Propen-2-yl)amino-7-methyl-pyrrolo[2,3d]pyrimidin-4-yl)-O-methyl-hydroxylamine (CLX), N-(2-n-Propylamino-7-methyl-pyrrolo[2,3d]pyrimidin-4-yl)-O,N-dimethyl-hydroxylamine (CLXII), N-(2-n-Propylamino-7-methyl-pyrrolo[2,3d]pyrimidin-4-yl)-O-methyl-hydroxylamine (CLXIV), N-(2-n-Propylamino-7-methyl-pyrrolo[2,3d]pyrimidin-4-yl)-hydrazine (CLXVI), N-Methyl-N-(2-n-propylamino-7-methyl-pyrrolo[2,3d]pyrimidin-4-yl)-hydrazine (CLXVIII), N,N-dimethyl-N'-(2-n-propylamino-7-methyl-pyrrolo[2,3d]pyrimidin-4-yl)-hydrazine (CLXX), a salt thereof and mixtures thereof. In another embodiment, the salt is hydrogen sulfate or hydrochloride.

In certain embodiments, the compound is selected from the group consisting of O,N-dimethyl-N-[4-(n-propylamino)-6-(prop-2-ynylamino-[1,3,5]triazin-2-yl]-hydroxylamine; N-methyl-N'-n-propyl-N"-prop-2-ynyl-[1,3,5]triazine-2,4,6-triamine; a salt thereof; and any combinations thereof.

In certain embodiments, the compound of Formula (I) is selected from compounds described in U.S. Pat. No. 9,162,992 and/or in U.S. Pat. No. 9,351,972 and/or in United States Patent Application Publication No. 2015-0291597, now abandoned, the teachings of which are incorporated by reference herein in their entirety.

In certain embodiments, the present disclosure is directed to a method for treating a disease or condition that is a neurological disorder by administering, to a patient in need thereof, an effective amount of a large-conductance potassium channel modulating compound. In certain embodiments, the present disclosure is directed to a method for treating a disease or condition that is a neurological disorder by administering, to a patient in need thereof, an effective amount of a large-conductance potassium channel modulating compound selected from compound(s) of Formula (I) as described herein. In certain embodiments, the neurological disorder is epilepsy, paroxysmal, dyskinesia, or schizophrenia. In certain embodiments, the neurological disorder is autism.

In certain embodiments, the present disclosure is directed to a method for treating a disease or a condition that is a cardiac disorder, such as, without limitations, cardiac ischemia or cardiac hypoxia. BK channels are extensively distributed in cardiovascular smooth muscle and cardiac fibroblasts, where they play a role as mediators of inflammation and in the remodeling of the heart following ischemic injury.

Multiple studies in animal models have suggested a role for BK channels in cardioprotection prior to and after reperfusion and ischemic injuries. Hence, in certain embodiments, the present disclosure is directed to a method for treating a disease or condition that is a cardiac disorder (such as, without limitations, cardiac ischemia or cardiac hypoxia) by administering, to a patient in need thereof, an effective amount of a large-conductance potassium channel modulating compound. In certain embodiments, the present disclosure is directed to a method for treating a disease or condition that is a cardiac disorder (such as, without limitations, cardiac ischemia or cardiac hypoxia) by administering, to a patient in need thereof, an effective amount of a large-conductance potassium channel modulating compound selected from compound(s) of Formula (I) as described herein.

In certain embodiments, the present disclosure is directed to a method for treating a disease or a condition that is a cerebral disorder, such as, without limitations, cerebral ischemia or cerebral hypoxia.

During ischemia-induced reduction in blood flow, critical supplies of oxygen and glucose to cells are impeded or stopped. This results in a decoupling of oxidative phosphorylation, reduced ATP levels, disruption of ionic flow, and disruption of normal ionic gradients. This leads to, for example, depolarization of cerebral cellular membranes, with resultant rapid influx of $Ca^{2+}$ and release of the excitatory amino acid, glutamate. Normally, glutamate is safely cleared from the synaptic cleft, but the processes are overwhelmed during ischemia. The excess glutamate in synaptic clefts binds to NMDA (N-methyl-D-aspartate) and AMPA (α-amino-3-hydroxy-5-methyl-4-isoxazolepropionic acid) receptors, producing a wave of depolarization that further propagates the ischemic damage. BK channels function as an "emergency brake" which limits calcium-induced glutamate release and NMDA activity, which occurs during cerebral ischemia.

Blood flow in the brain is closely regulated by a number of processes, but especially by neurovascular coupling. The component processes are controlled through coordinated activity of neurons, astrocytes, and parenchymal arterioles. Changes in localized blood flow ensures adequate oxygenation and nutrition to brain tissues. The cascade that begins and continues this process is complex, involving glutamate receptors on astrocytes, and potassium efflux mediated by BK channel subtypes on astrocyte endfeet. BK channel subtypes appear to be a prime mechanism in the transition from vasodilation in normal oxygenation of brain tissue, to vasoconstriction in the presence of blood consequent to a cerebral aneurysm rupture, worsening cerebral ischemia, and damage to cells.

BK channel subtypes may also play a role during cerebral ischemia from stroke other than aneurysmal bleed. Focal ischemia occurs due to the activity of BK channels on astrocytes increasing intracellular calcium and potassium efflux resulting in apoptotic and necrotic cellular death and reactive gliosis, all of which extend the damage from the initial ischemic event.

Hence, in certain embodiments, the present disclosure is directed to a method for treating a disease or condition that is a cerebral disorder (such as, without limitations, cerebral ischemia) by administering an effective amount of a large-conductance potassium channel modulating compound to a patient in need thereof. In certain embodiments, the present disclosure is directed to a method for treating a disease or condition that is a cerebral disorder (such as, without limitations, cerebral ischemia) by administering an effective amount of a large-conductance potassium channel modulating compound selected from compound(s) of Formula (I) as described herein to a patient in need thereof.

Hypoxia—an abnormally low level of oxygen pressure ($pO_2$) in arterial blood—is a principal physiological alerting signal for maintaining normal oxygen homeostasis. The body's response to hypoxia is reflexive and rapid (in the absence of respiratory-depressant influences), with the primary sensing organs (containing chemoceptors) being the carotid bodies at the bifurcation of the carotid arteries. Although similar sensors are found at the aortic arch and in the abdominal arteries, it is the carotid bodies that most respond to hypoxia. The carotid bodies also respond to increase in carbon dioxide ($pCO_2$) and decrease in pH. Under basal and normal conditions ($pO_2$~100 mmHg), sensory carotid body signaling is low. But signaling increases dramatically with even a small decrease in arterial blood $pO_2$, occurring within seconds. Hypoxia-sensitivity differs within a population of people, but is maintained within very close limits within a single individual. Human twin studies suggest a genetically-inherited determinant of sensitivity to hypoxia.

The response of the carotid body is relatively unusual in its sensitivity, speed, and lack of adaptation over time. One of the most powerful ligands and best characterized effectors of the BK channel is carbon monoxide (CO). CO activates BK channels via both direct and indirect mechanisms. The data suggest that the BK channels are activated in the presence of hypoxia, as a sort of negative-feedback loop. Once the carotid body is stimulated by hypoxia, a variety of strong ventilatory autonomic, cardiovascular, renal, and endocrine responses are elicited. Stimulation of BK channels in the carotid body induces neurotransmitter release and increased number of action potentials in the glossopharyngeal nerve. The impulse excites the nucleus of the solitary tract which targets brainstem circuits and stimulates respiratory response elements. The increase in respiratory response results in an increase in tidal volume (volume of air displaced between inhalation and exhalation) as well as the respiratory rate. Due to normal cardiopulmonary coupling, there is a concomitant increase in cardiac output. The hypoxic drive is strong enough to stimulate breathing even during hypocapnic apneas, such as occurs during opioid-induced respiratory depression and opioid overdose.

Hence, in certain embodiments, the present disclosure is directed to a method for treating a hypoxia and/or a hypercapnia-reduced respiratory function by administering an effective amount of a large-conductance potassium channel modulating compound to a patient in need thereof. In certain embodiments, the present disclosure is directed to a method for treating a hypoxia and/or a hypercapnia-reduced respiratory function by administering an effective amount of a large-conductance potassium channel modulating compound selected from Formula (I) as described herein to a patient in need thereof.

In certain embodiments, the present disclosure is directed to a method for treating a disease or condition that is a cerebral disorder (such as, without limitations, cerebral hypoxia) by administering an effective amount of a large-conductance potassium channel modulating compound to a patient in need thereof. In certain embodiments, the present disclosure is directed to a method for treating a disease or condition that is a cerebral disorder (such as, without limitations, cerebral hypoxia) by administering an effective amount of a large-conductance potassium channel modulating compound selected from Formula (I) as described herein to a patient in need thereof.

Further, BK channels have also been shown to be involved in the regulation of airway surface liquid (ASL) homeostasis, and therefore mucociliary clearance (MCC), both important innate host defense mechanisms. In disease states where ASL volume is reduced and pathology ensues, targeting BK channels may be a viable pharmacologic target.

Hence, in certain embodiments, the present disclosure is directed to a method for treating a disease or a condition where ASL volume is reduces and pathology ensues by administering an effective amount of a large-conductance potassium channel modulating compound to a patient in need thereof. In certain embodiments, the present disclosure is directed to a method for treating a disease or a condition where ASL volume is reduces and pathology ensues by administering an effective amount of a large-conductance potassium channel modulating compound selected from Formula (I) as described herein to a patient in need thereof.

In certain embodiments, the present disclosure is directed to a method for treating a disease or condition that requires organ protection by administering an effective amount of a large-conductance potassium channel modulating compound to a patient in need thereof. In certain embodiments, the present disclosure is directed to a method for treating a disease or condition that requires organ protection by administering an effective amount of a large-conductance potassium channel modulating compound selected from compound(s) of Formula (I) as described herein to a patient in need thereof. In certain embodiments, the organ protection is one or both of cerebro- and cardio-protection against ischemia and/or hypoxia and/or stimulation of respiration in the presence of such conditions (both local and systemic).

In certain embodiments, the present disclosure is directed to a method stimulating respiration by administering an effective amount of a large-conductance potassium channel modulating compound to a patient in need thereof. In certain embodiments, the present disclosure is directed to a method stimulating respiration by administering an effective amount of a large-conductance potassium channel modulating compound selected from compound(s) of Formula (I) as described herein to a patient in need thereof.

In certain embodiments, the present disclosure is directed to a method counteracting an effect of a respiratory depressant (e.g., opioid, benzodiazepine, isoflurane, and propofol) by administering an effective amount of a large-conductance potassium channel modulating compound to a patient in need thereof. In certain embodiments, the present disclosure is directed to a method counteracting an effect of a respiratory depressant (e.g., opioid, benzodiazepine, isoflurane, and propofol) by administering an effective amount of a large-conductance potassium channel modulating compound selected from compound(s) of Formula (I) as described herein to a patient in need thereof. In certain embodiments, the method for stimulating respiration and/or counteracting an effect of a respiratory depressant is performed on a subject that is experiencing an overdose and/or effects of a respiratory depressant. In certain embodiments, the method for stimulating respiration is performed on a subject that is experiencing respiratory depression due to a bacterial or a viral infection or due to symptoms related to the bacterial or viral infection.

Example opioids include, without limitations, any natural or synthetic opioid analgesic, such as morphine, fentanyl, codeine, thebaine, diacetylmorphine (heroin), dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levoalphacetylmethadol (LAAM), loperamide, diphenoxylate, pentazocine, phenazocine, buprenorphine, etorphine, butorphanol, nalbuphine, levorphanol, levomethorphan, dezocine, lefetamine, tilidine, tramadol, propoxyphene, and oxycodone. As intended herein, an opioid also encompasses any natural or synthetic narcotic antagonist such as nalmefene, naloxone or naltrexone as well as any natural or synthetic mixed opioid agonist/antagonist such as nalbuphine, butorphanol, buprenorphine and pentazocine.

Example benzodiazepines include, without limitations, diazepam, chlordiazepoxide, alprazolam, triazolam, estazolam, clonazepam, flunitrazepam, pharmaceutically acceptable salts thereof, and the like.

In certain embodiments, the present disclosure is directed to a method for treating diabetic complications and/or bladder dysfunctions by administering an effective amount of a large-conductance potassium channel modulating compound to a patient in need thereof. In certain embodiments, the present disclosure is directed to a method for treating diabetic complications and/or bladder dysfunctions by administering an effective amount of a large-conductance potassium channel modulating compound selected from compound(s) of Formula (I) as described herein to a patient in need thereof.

In certain embodiments, the present disclosure is directed to a method for treating ocular hypertension by administering an effective amount of a large-conductance potassium channel modulating compound to a patient in need thereof. In certain embodiments, the present disclosure is directed to a method for treating ocular hypertension by administering an effective amount of a large-conductance potassium channel modulating compound selected from compound(s) of Formula (I) as described herein to a patient in need thereof.

In certain embodiments, the large-conductance potassium channel, modulated by the compound of Formula (I), is located at one or both of a pre-synaptic or post-synaptic site. In certain embodiments, the large-conductance potassium channel, modulated by the compound of Formula (I), is located at one or both of cardiovascular smooth muscle and cardiac fibroblasts. In certain embodiments, the large-conductance potassium channel, modulated by the compound of Formula (I), is located at one or both of airway surface liquid and mucociliary clearance.

In certain embodiments, the compound of Formula (I) is an agonist. In certain embodiments, the compound of Formula (I) is an antagonist. In certain embodiments, the compound of Formula (I) modulates at one or both of the pore gate or the voltage sensing domain of the large-conductance potassium channel. In certain embodiments, the compound of Formula (I) modulates at one or both of the RCK1 or the RCK2 of the large-conductance potassium channel.

The term "modulator," as used herein, is any ligand that binds to one or more components of the BK channel and thus alters (e.g., by inhibiting or activating) the proportion of the BK channels, which are in active form, resulting in a biological response.

The term "agonist," as used herein, is any ligand that that binds to one or more components of the BK channel and thus activates the BK channel or increases the proportion of the BK channels, which are in active form, resulting in a biological response.

The term "antagonist," as used herein, is any ligand that binds to one or more components of the BK channel and thus inhibits the BK channel or decreases the proportion of the BK channels, which are in active form, resulting in a biological response.

In certain embodiments, the method may include administering any of the compounds described herein in combination with at least one additional active agent, which may be administered simultaneously, sequentially, or concurrently. In certain embodiments, the two agents are administered sequentially such that there is an overlap of the therapeutic interval provided by each agent. With sequential administration, the agents are in separate dosage forms and can be administered by the same route of administration (e.g., pulmonary) or by different routes of administration (e.g., parenteral and pulmonary). Suitable routes of administration for the one or more active agents (i.e., the BK channel modulator and additional active agent) may be independently selected from oral, intravenous (e.g., continuous infusion or bolus injection), nasal, inhalational, topical, buccal, rectal, pleural, peritoneal, vaginal, intramuscular, subcutaneous, transdermal, epidural, intratrachael (e.g., intratracheal instillation or intratracheal inhalation), otic, intraocular, or intrathecal route. Non-limiting exemplary suitable pulmonary administration may be with a metered dose inhaler, nebulizer, soft mist inhaler, a high efficiency nebulizer, ultrasonic nebulizer, dry powder inhaler, a continuous positive airway pressure (CPAP) machine, a bilevel positive airway pressure machine (BiPAP), or a ventilator.

The term "simultaneously" as used herein means that a dose of one agent is administered at the same time as another agent, regardless of whether the agents are administered separately via the same or different routes of administration or in a single pharmaceutical composition or dosage form.

The term "sequentially" as used herein means that a dose of one agent is administered first and thereafter a dose of another agent is administered second.

The term "concurrent," as used herein, refers to an overlap in the therapeutic window of the BK channel modulator and the additional active agent. The two active agent(s) can be administered simultaneously, but simultaneous administration is not required.

Composition

In certain embodiments, the instant disclosure is directed to a pharmaceutical composition suitable for treating a disease or a condition modulated by large-conductance potassium channels. In certain embodiments, the pharmaceutical composition includes a therapeutically effective amount of a large-conductance potassium channel modulating of a compound selected from Formula (I):

(I)

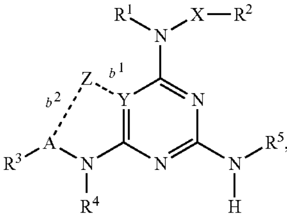

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

In certain embodiments, the instant disclosure is directed to a pharmaceutical composition suitable for treating a disease or a condition modulated by large-conductance potassium channels. In certain embodiments, the pharmaceutical composition includes a therapeutically effective amount of a large-conductance potassium channel modulating of a compound selected from Formula (I):

(I)

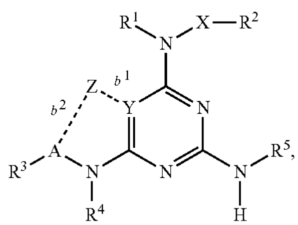

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl; wherein at least one substituent selected from the group consisting of $R^1$, $R^2$, $R^3$ and $R^5$ is alkynyl or substituted alkynyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

In certain embodiments, the instant disclosure is directed to a pharmaceutical composition suitable for treating a disease or a condition modulated by large-conductance potassium channels. In certain embodiments, the pharmaceutical composition includes a therapeutically effective amount of a large-conductance potassium channel modulating of a compound selected from Formula (I):

(I)

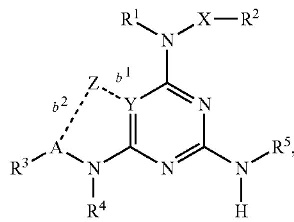

wherein:

$R^1$ and $R^2$ are independently H, alkyl, substituted alkyl, cycloalkyl, substituted cycloalkyl, alkenyl, substituted alkenyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, cycloalkyl, substituted cycloalkyl, alkenyl, substituted alkenyl, —$NR^1R^2$, —$C(O)OR^1$, acyl, or aryl;

$R^4$ is H, alkyl, or substituted alkyl;

$R^5$ is H, alkyl, substituted alkyl, cycloalkyl, substituted cycloalkyl, alkenyl, substituted alkenyl, —$OR^1$, —$NR^1R^2$, —$C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

In certain embodiments, the instant disclosure is directed to a pharmaceutical composition suitable for treating a disease or a condition modulated by large-conductance potassium channels. In certain embodiments, the pharmaceutical composition includes a therapeutically effective amount of a large-conductance potassium channel modulating of a compound selected from Formula (I):

(I)

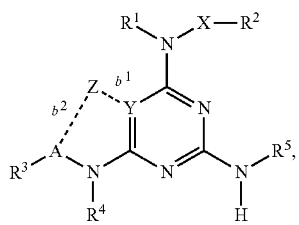

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl or substituted alkynyl;

$R^4$ is H, alkyl, or substituted alkyl;

$R^5$ is alkyl, propargylic, substituted propargylic, homopropargylic, or substituted homopropargylic, wherein at least one substituent selected from the group consisting of $R^1$, $R^2$, $R^3$ and $R^5$ is alkynyl or substituted alkynyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and:

(i) Z is H, bond $b^2$ is a single bond, and A is CH; or, (ii) Z is nil, bond $b^2$ is nil, and A is a single bond; and, if Y is C, then bond $b^1$ is a single bond, and:

(i) Z is $CH_2$, bond $b^2$ is a single bond, and A is CH; or, (ii) Z is CH, bond $b^2$ is a double bond, and A is C;

or a salt thereof.

In one embodiment, the at least one compound of formula (I) is selected from the group consisting of (i) Y is N, bond b1 is nil, Z is H, bond $b^2$ is a single bond, A is CH, and the at least one compound is a compound of formula (II-a) or a salt thereof:

(II-a)

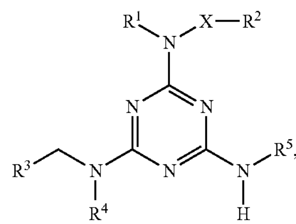

and (ii) Y is N, bond b1 is nil, Z is nil, bond $b^2$ is nil, and A is a bond, and the compound of the invention is a compound of formula (II-b) or a salt thereof:

(II-b)

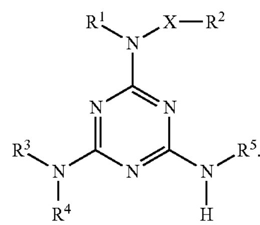

In one embodiment, the at least one compound of formula (I) is selected from the group consisting of: (i) Y is $CR^6$, bond $b^1$ is nil, Z is H, bond $b^2$ is a single bond, A is CH, and the at least one compound is a compound of formula (III-a) or a salt thereof:

(III-a)

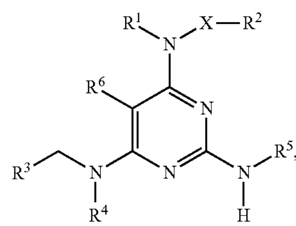

and (ii) Y is $CR^6$, bond $b^1$ is nil, Z is nil, bond $b^2$ is nil, and A is a bond, and the compound of the invention is a pyrimidine of formula (III-b) or a salt thereof:

(III-b)

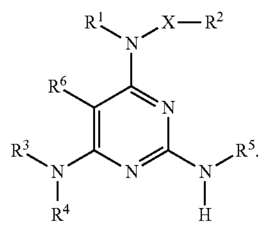

In one embodiment, Y is C, bond $b^1$ is a single bond, Z is $CH_2$, bond $b^2$ is a single bond, A is CH, and said at least one compound is a compound of formula (IV) or a salt thereof:

(IV)

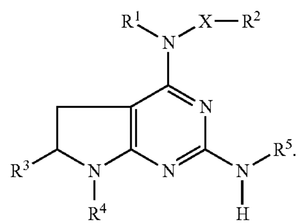

In one embodiment, Y is C, bond b is a single bond, Z is CH, bond $b^2$ is a double bond, A is C, and said at least one compound is a compound of formula (V) or a salt thereof:

(V)

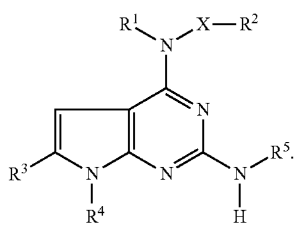

In one embodiment, the at least one compound is selected from the group consisting of: N-(4,6-Bis-methylamino-[1,3,5]triazin-2-yl)-N,O-dimethyl-hydroxylamine (XX), N-(4,6-Bis-ethylamino-[1,3,5]triazin-2-yl)-N,O-dimethyl-hydroxylamine (XXII), N-(4-Cyclopropylmethylamino)-N-(6-n-propylamino) [1,3,5]triazin-2-yl)-N,O-dimethyl-hydroxylamine (XXV), N-(4-Ethylamino)-N-(6-n-propylamino)-[1,3,5]triazin-2-yl)-N,O-dimethyl-hydroxylamine (XXVII), N-(Bis-4,6-(2-methylpropylamino)) [1,3,5]triazin-2-yl)-N,O-dimethyl-hydroxylamine (XXIX), N-(Bis-4,6-(2,2-dimethylpropylamino)) [1,3,5]triazin-2-yl)-O,N-dimethyl-hydroxylamine (XXXI), 4,6-Bis-N-cyclopropylamino-[1,3,5]triazin-2-yl)-N,O-dimethyl-hydroxylamine hydrochloride (XXXIII), N-(4,6-Bis-n-propylamino-[1,3,5]triazin-2-yl)-O,N-dimethyl-hydroxylamine (XXXV), N-(4-(Methoxy(methyl)amino)-6-(propylamino)-1,3,5-triazin-2-yl)propionamide (XL), N-(4,6-Bis-propylamino-[1,3,5]triazin-2-yl)-O-methyl-hydroxylamine (XLI), O-Allyl-N-(4,6-bis-propylamino-[1,3,5]triazin-2-yl)-hydroxylamine (XLIII), N-(4,6-Bis-propylamino-[1,3,5]triazin-2-yl)-hydroxylamine (XLV), 6-(Methoxy(methyl)amino)-N2-propyl-1,3,5-triazine-2,4-diamine (XLVII), N-(4,6-Bis-propylamino-[1,3,5]triazin-2-yl)-N-methyl-hydroxylamine (XLVIII), O-Benzyl-N-(4,6-bis-propylamino-[1,3,5]triazin-2-yl)-N-methyl-hydroxylamine (LIII), N-(4,6-Bis-propylamino-[1,3,5]triazin-2-yl)-N-isopropyl-hydroxylamine (LV), 6-[1,2]Oxazinan-2-yl-N,N'-dipropyl-[1,3,5]triazine-2,4-diamine (LVII), N-(4,6-Bis-propylamino-[1,3,5]triazin-2-yl)-O-isopropyl-N-methyl-hydroxylamine (LXIV), O-Benzyl-N-(4,6-bis-propylamino-[1,3,5]triazin-2-yl)-N-ethyl-hydroxylamine (LXVIII), N-(4,6-Bis-propylamino-[1,3,5]triazin-2-yl)-O-isopropyl-hydroxylamine (LXX), 6-((Benzyloxy)(isopropyl)amino)-N2,N4-dipropyl-1,3,5-triazine-2,4-diamine (LXXII), N-(4,6-Bis-propylamino-[1,3,5]triazin-2-yl)-N-ethyl-O-isopropyl-hydroxylamine (LXXVI), N-(4,6-Bis-propylamino-[1,3,5]triazin-2-yl)-O-isobutyl-N-methyl-hydroxylamine (LXXXII), 6-(Methyl(thiophen-2-ylmethoxy)amino)-N2,N4-dipropyl-1,3,5-triazine-2,4-diamine (LXXXIV), N-(4,6-Bis-propylamino-[1,3,5]triazin-2-yl)-O-cyclopropylmethyl-N-methyl-hydroxylamine (XCI), N-(4,6-Bis-propylamino-[1,3,5]triazin-2-yl)-O-ethyl-N-methyl-hydroxylamine (XCVI), N-(4,6-Bis-propylamino-[1,3,5]triazin-2-yl)-O-(2,2-difluoro-ethyl)-hydroxylamine (C), 4-N-(2-Dimethylaminoethyl)amino-6-N-(n-propyl)amino-[1,3,5]triazin-2-yl)-N,O-dimethyl-hydroxylamine (CIII), 4-N-(3-(1-N-Methylimidazol-2-yl)-propyl)-amino-6-N-(n-propyl)amino-[1,3,5]triazin-2-yl)-N,O-dimethyl-hydroxylamine (CV), 4-N-(1-N-Methylimidazol-2-yl)-methylamino-6-N-(n-propyl)amino-[1,3,5]triazin-2-yl)-O,N-dimethyl-hydroxylamine (CVII), 4,6-Bis-(N-(2-dimethylaminoethyl)amino)-[1,3,5]triazin-2-yl)-N,O-dimethyl-hydroxylamine (CIX), 4,6-Bis-(N-(pyridin-4-ylmethyl)amino)-[1,3,5]triazin-2-yl)-N,O-dimethyl-hydroxylamine (CXI), 4,6-Bis-[N-(3-methoxy-n-propyl)amino]-[1,3,5]triazin-2-yl)-N,O-dimethyl-hydroxylamine (CXIII), 4,6-Bis-[N-(tetrahydropyran-4-ylmethyl)amino]-[1,3,5]triazin-2-yl)-N,O-dimethyl-hydroxylamine (CXV), N-(5,8,11-Trioxa-2,14,16,18,19-pentaazabicyclo[13.3.1]-nonadeca-1(18),15(19),16(17)-trien-17-yl)-N,O-dimethyl-hydroxylamine (CXVII), N-(4,6-Bis-propylamino-[1,3,5]triazin-2-yl)-N',N'-dimethylhydrazine (XLVI), N-(4,6-Bis-propylamino-[1,3,5]triazin-2-yl)-N-methyl-N'-methylhydrazine (XLIX), a salt thereof and mixtures thereof. In another embodiment, the salt is hydrogen sulfate or hydrochloride.

In one embodiment, the at least one compound is 2,6-bis-(N-n-propylamino)-[1,3]pyrimidin-4-yl)-N,O-dimethyl-hydroxylamine N-(4-(Methoxy(methyl)amino)-6-(propylamino)-1,3,5-triazin-2-yl)propionamide or a salt thereof. In another embodiment, the salt is hydrogen sulfate or hydrochloride.

In one embodiment, the at least one compound is N-(4-(Methoxy(methyl)amino)-6-(propylamino)-1,3,5-triazin-2-yl)propionamide or a salt thereof. In another embodiment, the salt is hydrogen sulfate or hydrochloride.

In one embodiment, the at least one compound is selected from the group consisting of: 2-(n-Propyl)amino-4-(i-propylamino-7-methyl-pyrrolidino[2,3-d]pyrimidine (CXXVI), 2-(n-Propyl)amino-4-dimethylamino-7-methyl-pyrrolidino[2,3-d]pyrimidine (CXXVIII), 2-(n-Propyl)amino-4-methylamino-7-methyl-pyrrolidino[2,3-d]pyrimidine (CXXXI), 2-(n-Propyl)amino-4-(i-propyl)amino-7-i-propyl-pyrrolidino[2,3-d]pyrimidine (CXXXVI), 2,4-Bis-(n-propyl)amino-7H-pyrrolidino[2,3-d]pyrimidine (CXLIX), 2-(n-Propyl)amino-4-(4-hydroxypiperidin-1-yl)-7-methyl-pyrrolidino[2,3-d]pyrimidine (CLII), 8-(7-Methyl-2-(propylamino)-pyrrolidino[2,3-d]pyrimidin-4-yl)-8-azabicyclo[3.2.1]octan-3-ol (CLV), a salt thereof and mixtures thereof. In another embodiment, the salt is hydrogen sulfate or hydrochloride.

In one embodiment, the at least one compound is selected from the group consisting of: N-(2-Propylamino-7H-pyrrolo[2,3d]pyrimidin-4-yl)-O,N-dimethyl-hydroxylamine (CXLI), N-(2-(Propen-2-yl)amino-7-methyl-pyrrolo[2,3d]pyrimidin-4-yl)-N,O-dimethyl-hydroxylamine (CLVIII), N-(2-(Propen-2-yl)amino-7-methyl-pyrrolo[2,3d]pyrimidin-4-yl)-O-methyl-hydroxylamine (CLX), N-(2-n-Propylamino-7-methyl-pyrrolo[2,3d]pyrimidin-4-yl)-O,N-dimethyl-hydroxylamine (CLXII), N-(2-n-Propylamino-7-methyl-pyrrolo[2,3d]pyrimidin-4-yl)-O-methyl-hydroxylamine (CLXIV), N-(2-n-Propylamino-7-methyl-pyrrolo[2,3d]pyrimidin-4-yl)-hydrazine (CLXVI), N-Methyl-N-(2-n-propylamino-7-methyl-pyrrolo[2,3d]pyrimidin-4-yl)-hydrazine (CLXVIII), N,N-dimethyl-N'-(2-n-propylamino-7-methyl-pyrrolo[2,3d]pyrimidin-4-yl)-hydrazine (CLXX), a salt thereof and mixtures thereof. In another embodiment, the salt is hydrogen sulfate or hydrochloride.

In certain embodiments, the compound of Formula (I) is selected from compounds described in U.S. Pat. No. 9,162,992 and/or in U.S. Pat. No. 9,351,972 and/or in United States Patent Application Publication No. US 2015-0291597, now abandoned, the teachings of which are incorporated by reference herein in their entirety.

In certain embodiments, the pharmaceutical compositions include a single dose of the BK channel modulating compound, where a single dose includes a therapeutically effective amount of the BK channel modulating compound to treat a condition or a disease modulated by a BK channel. In certain embodiments, the pharmaceutical compositions include a plurality of doses of the BK channel modulating compound (e.g., two or more, three or more, four or more, etc).

In certain embodiments, the pharmaceutical composition comprises a BK channel modulating compound and one or more additional active agents.

In certain embodiments, the active agent(s) in the pharmaceutical composition (e.g., a BK channel modulating compound and optionally one or more additional active agents) is/are lyophilized.

In certain embodiments, the pharmaceutical composition is pre-mixed (e.g., an active agent is pre-mixed with one or more pharmaceutically acceptable excipients and optionally with one or more additional active agents).

In certain embodiments, the pharmaceutical composition may be contained in a glass container or in a plastic container.

In certain embodiments, the pharmaceutical composition further comprises one or more pharmaceutically acceptable excipient. Suitable pharmaceutically acceptable excipients may vary based on the final form and route of administration of the composition.

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, intraperitoneal, intrathoracic, intrapleural and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

In certain embodiments, pharmaceutically acceptable excipients include a pharmaceutically acceptable carrier, such as, a liquid or solid filler, stabilizer, dispersing agent, suspending agent, diluent, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like.

Examples of preservatives useful in accordance with the invention included but are not limited to those selected from the group consisting of benzyl alcohol, sorbic acid, parabens, imidurea and combinations thereof.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

In certain embodiments, the one or more additional excipients includes a pH adjusting agent, which may be selected from sodium hydroxide, potassium hydroxide, calcium hydroxide, ammonium hydroxide, sulfuric acid, phosphoric acid, nitric acid, sodium citrate, sodium acetate, magnesium hydroxide, citric acid, hydrochloric acid, or a mixture thereof.

In certain embodiments, the composition may include one or more additional excipients, such as, without limitations, carbohydrates, antioxidants, chelating agents, low-molecular weight proteins, high-molecular weight polymers, gel-forming agents, stabilizers, additives, wetting agents, emulsifying agents, surfactant and/or dispersing agents, alkalizing agents, coloring agents, synthetic dies, fillers, diluents, mineral oxides, preservatives, or a mixture thereof.

In certain embodiment, the composition further includes an antioxidant. In certain embodiments, the antioxidant may include trivalent phosphorous like e.g phosphite, phenolic antioxidants, hydroxylamines, lactones such as substituted benzofuranones. Hindered phenols, thiosynergists and/or hindered amines are useful for the long-term stability for polymers, whereas the following antioxidants are suitable for use also in situation where the active substance is subject to oxidation: acids (ascorbic acid, erythorbic acid, etidronic acid, gallic acid, hypophosphorous acid, nordihydroguairetic acid, propionic acid etc.), phenols (e.g. BHA, BHT, t-butyl hydroquinone, dodecyl gallate, octyl gallate, 1,3,5-trihydroxybenzene), organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopherol acetate, d-α-tocopheryl acetate, dl-α-tocopheryl acetate. However, other anti-oxidative agents known in the art may be used according to the present invention.

In certain embodiments, suitable antioxidants may include, without limitations, sterically hindered phenols, aryl amines, thioureas, thiocarbamates, phosphites, thioether esters, and combinations of the foregoing. Other suitable examples of antioxidants include, but are not limited to, alkylated monophenols, including but not limited to, 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1-yl)phenol and mixtures thereof, alkylthiomethylphenols, including but not limited to, 2,4-dioctylthiomethyl-6-tert-hutylphenol, 2,4-dioctylthiomethyl-6-methylphenol, 2,4-dioetylthiomethyl-6-ethylphenol, 2,6-di-dodecylthiomethyl-4-nonylphenol, hydroquinones and alkylated hydroquinones, including but not limited to, 2,6-di-tert-hutyl-4-methoxyphenol, 2,5-di-tert-butylhydroquinone, 2,5-di-tort-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate, tocopherols, including but not limited to, α-tocopherol, j3-tocopherol, γ-tocopherol, 6-tocopherol and mixtures thereof (vitamin E), hydroxylated thiodiphenyl ethers, including but not limited to, 2,2'-thiobis(6-tort-butyl-4-methylphenol), 2,2'-thiobis(4-oetylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide, alkylidenebisphenols, including but not limited to, 2,2'-methylenebis(6-tert-butyl-4-methylphenol), 2,2'-methylenebis(6-tert-butyl-4-ethylphenol), 2,2'-methylenebis[4-methyl-6-((α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-test-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,5,5-tetra-(5-tert-butyl-4-hydroxy-2-methylphenyl)pentane, O-, N- and S-benzyl compounds, including but not limited to, 3,5,3',5'-tetra-tert-butyl.-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate, hydroxybenzylated malonates, including but not limited to, dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate, aromatic hydroxybenzyl compounds, including but not limited to, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol, triazine compounds, including but not limited to, 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxy-phenylpropionyl)-hexahydro-1,3,5-triazine, 1,3,5-tris(3,5-dicyclohexyl-4-hydroxybenzyl)iso-cyanurate, benzylphosphonates, including but not limited to, dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid, acylaminophenols, including but not limited to, 4-hydroxylauranilide, 4-hydroxystearanilide, octyl N-(3,5-di-tert-butyl-4-hydroxyphenyl)carbamate, esters of β-(3,5-di-tert-butyl-4-hydroxyphenyl)propionic acid with mono- or polyhydric alcohols, e.g. with methanol, ethanol n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane, esters of 6-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2,2]octane, esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycal, thiodiethyl.ene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, amides of 6-(3,5-di-tert-butyl-4-hydroxyphenyl)propionic acid e.g. N,N'-bis(3,5-di-tert-butylA-hydroxyphenylpropionyl) hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy) ethyl]oxamide (Naugard®XL-1, supplied by Uniroyal), ascorbic acid (vitamin C), aminic antioxidants, including but not limited to, N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenyienediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, including but not limited to, p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated teak-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene, and combinations of the foregoing.

In certain embodiments, suitable pharmaceutically acceptable excipients may include acrylics, cellulose derivatives, polysaccharides, monosaccharides, gums, natural or synthetic polymers (e.g., polyalkylene oxides (e.g., polymethylene oxides, polyethylene oxides, polypropylene oxides) polyethylenes, polypropylenes, polyvinyl chlorides, polycarbonates, polystyrenes, polyacrylates, polycaprolactone, polymethacrylates copolymers thereof, and mixtures thereof), liposomes, disintegrants (e.g., polyvinylpyrrolidone, sodium starch glycolate, crosscarmellose sodium, or a mixture thereof), glidants, lubricants, absorption enhancers, surfactants, binders, softeners, plasticizers (e.g., lecithin, hydrogenated vegetable oils, glycerol ester, lanolin, methyl ester, pentaerythritol ester, rice bran wax, stearic acid, sodium potassium stearates, and the like), waxes, fats, emulsifiers, fillers, antioxidants, flavors, colorants, diluents, processing aids (e.g., granulating aids), sweeteners such as those described above with respect to the chewable composition, fixing agents (e.g., polyols such as, without limitations, sorbitol, maltitol/isomalt, mannitol, starch, and the like), pH-adjusting agents, viscosity adjusting agents, solubility increasing or descreasing agents, osmotic agents, solvents, or a combination thereof.

In certain embodiments, suitable pharmaceutically acceptable excipients may include polyvinylpyrrolidone, natural and synthetic gums, polyvinyl alcohol, corn starch, hydrophilic and hydrophobic materials such as sustained release polymers, acrylic resins, protein-derived materials, waxes, shellacs, and solid or semi-solid oils such as hydrogenated castor oil and hydrogenated vegetable oil. More specifically, the controlled release materials can be, e.g., alkylcelluloses such as ethylcellulose, acrylic and methacrylic acid polymers and copolymers (e.g., acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, poly (methyl methacrylate), poly(methyl methacrylate) copolymer, polyacrylamide, aminoalkyl methacrylate copolymer, poly(methacrylic acid anhydride), glycidyl methacrylate copolymers, and mixtures of any of the foregoing), and cellulose ethers, such as hydroxyalkylcelluloses (e.g., hydroxypropylmethylcellulose) and carboxyalkylcelluloses. Waxes include, e.g., natural and synthetic waxes, fatty acids, fatty alcohols, and mixtures of the same (e.g., beeswax, carnauba wax, stearic acid and stearyl alcohol).

In certain embodiments, suitable pharmaceutically acceptable excipients may include gelling agents, such as and without limitation, sugars or sugar derived alcohols, such as mannitol, sorbitol, and the like, starch and starch derivatives, cellulose derivatives (such as microcrystalline cellulose, sodium caboxymethyl cellulose, methylcellulose, ethyl cellulose, hydroxyethyl cellulose, hydroxypropyl cellulose, hydroxypropyl methylcellulose, cellulose esters, cellulose diesters, cellulose triesters, cellulose ethers, cellulose ester-ethers, cellulose acylates, cellulose diacylates, cellulose triacylates, cellulose acetates, cellulose diacetates, cellulose triacetates, cellulose acetate propionates, cellulose acetate butyrates, cellulose acetate succinate, cellulose acetate phthalate, hydroxypropyl methyl cellulose phthalate, hydroxy propyl methyl cellulose acetate succinate (hypermellose acetate succinate), and mixtures thereof), attapulgites, bentonites, dextrins, alginates, algenic acid salts such as sodium alginate and potassium alginate, casein, stearic acid, shellac, carrageenan, gum tragacanth, gum acacia, gum arabic, pullulan gum, dextrin, gellan gum, agar gum, tara gum, karaya, guar gum, welan gum, rhamsan gum, locust bean gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof.

In certain embodiments, suitable pharmaceutically acceptable excipients may include hydrophilic excipients, such as without limitations, water, low molecular weight polyols, such as, polyethylene glycol, polypropylene glycol, or a combination thereof. Examples of other suitable hydrophilic carriers include, without limitations, polyoxyethylene derivatives of a sorbitan ester, such as sorbitan monolaurate (Polysorbate 20), Polysorbate 80, Polysorbate 60, polyoxyethylene 20 sorbitan trioleate (Polysorbate 85), acetic acid, formic acid, other hydrophilic surfactants and mixtures thereof. Exemplary low molecular weight polyols include, without limitations, those having a number average molecular weight of from any of about 200 Dalton, about 400 Dalton, about 600 Dalton, about 800 Dalton, or about 1000 Dalton to any of about 2000 Dalton, about 3000 Dalton, about 4000 Dalton, about 5000 Dalton, about 6000 Da, or about 7000 Da, or any sub-range or single value therein (for instance, polyethylene glycol 400, polyethylene glycol 600, or the like).

In certain embodiments, suitable pharmaceutically acceptable excipients may include plasticizers, such as, but not be limited to, sugar alcohol plasticizer such as triacetin, isomalt, maltitol, xylitol, erythritol, adonitol, dulcitol, pentaerythritol, or mannitol; or polyol plasticizer such as diglycerin, ethylene glycol, diethylene glycol, triethyleneglycol, tetraethylene glycol, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In certain embodiments, suitable pharmaceutically acceptable excipients may include plasticizer such as, without limitations, phosphate esters; phthalate esters; amides; mineral oils; fatty acids and esters; fatty alcohols, vegetable oils and hydrogenated vegetable oils including acetylated hydrogenated cottonseed glyceride and acetylated hydrogenated soybean oil glycerides; acetyl tributyl citrate, acetyl triethyl citrate, Castor oil, diacetylated monoglycerides, dipropylene glycol salicylate glycerin, glyceryl cocoate, mono- and di-acetylated monoglycerides, nitrobenzene, carbon disulfide, fl-naphtyl salicylate, phthalyl glycolate, diocyl phthalate; sorbitol, sorbitol glyceryl tricitrate; sucrose octaacetate; a-tocopheryl polyethylene glycol succinate, phosphate esters; phthalate esters; amides; mineral oils; fatty acids and esters; fatty alcohols; and vegetable oils, fatty alcohols including cetostearyl alcohol, cetyl alcohol, stearyl alcohol, oleyl alcohol and myristyl alcohol; methyl abietate, acetyl tributyl citrate, acetyl triethyl citrate, diisooctyl adipate, amyl oleate, butyl ricinoleate, benzyl benzoate, butyl and glycol esters of fatty acids, butyl diglycol carbonate, butyl oleate, butyl stearate, di(beta-methoxyethyl) adipate, dibutyl sebacate, dibutyl tartrate, diisobutyl adipate, dihexyl adipate, triethylene glycol di(beta-ethyl butyrate), polyethylene glycol di(2-ethyl hexoate), diethylene glycol monolaurate, monomeric polyethylene ester, hydrogenated methyl ester of rosin, methoxyethyl oleate, butoxyethyl stearate, butyl phthalyl butyl glycolate, glycerol tributyrate, triethylene glycol dipelargonate, beta-(p-tert-amyl phenoxy) ethanol, beta(p-tert-butytphenoxy)ethanol, beta-(p-tert-butytphenoxyethyl)acetate, bis(beta-p-tert-buthylphenoxydiethyl)ether, camphor, Cumar W-1, Cumar MH-1, Cumar V-1, diamyl phthalate, (diamylphenoxy) ethanol, diphenyl oxide, technical hydroabietyl alcohol, beckolin, benzene hexahydrochlonde, Clorafin 40, Piccolastic A-5, Piccalastic A-25, Flexol B-400, Glycerol alfa-methyl alfa-phenyl ether, chlorinated naphthalene, HB-40, monoamylphthalate. Nevillac 10 o-nitrodiphenyl and Paracril 26.

In certain embodiments, suitable pharmaceutically acceptable excipients may include plasticizer such as, without limitations, sugar alcohol plasticizer such as isomalt, maltitol, sorbitol, xylitol, erythritol, adonitol, dulcitol, pentaerythritol, or mannitol; or polyol plasticizer such as glycerin, diglycerin, ethylene glycol, diethylene glycol, triethyleneglycol, tetraethylene glycol, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In certain embodiments, suitable pharmaceutically acceptable excipients may include fragrances such as, without limitations, natural and/or synthetic fragrance raw materials. For instance, oil soluble perfume oils, which may or may not be in mixture with water soluble perfume oils. Oil soluble perfume materials are natural, or natural-identical essential oils such as orange oil, lavender oil, pine oil, *eucalyptus* oil, lemon oil, clove leaf, peppermint oil, cedarwood oil, rosemary oil, bergamot oil, lavandin oil, patchouli oil, chamomile oil, jasmine oil, spike oil, rose oil, Vetiver oil, fennel oil, anise oil, thyme oil, germanium oil, menthol, and marjoram oil. An animal fragrance is for example musk, castoreum, aber or zibet. Spagyric essences are also known in the art. They are made by fermenting certain herbs that are then processed to the final product. Synthetic fragrance ingredients are for example synthetic essential oils such as composed of single compounds such as linalol, terpineol, nerol, citronellal, benzaldehyde, cinnamon aldehyde, vanillin, ethylvanillin, or methylacetophenone. The fragrance materials may also be synthetic oil soluble perfume oils selected from the usual group consisting of fragrant hydrocarbons, alcohols, ketones, aldehydes, ethers, esters, polyene derivatives. Other fragrances that may be used are catalogued and described in references and databases such as S. Arctander, Perfume and Flavor Chemicals, Volumes I and II (1960, 1969; reprint 2000); Allured's Flavor and Fragrance Materials (2005); and database maintained by the Research Institute for Fragrance Materials at www.rifm.org.

In certain embodiments, suitable pharmaceutically acceptable excipients may include a perfume oil. Suitable perfume oils include mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, *angelica*, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (*galbanum*, elemi, benzoin, myrrh, olibanum, opoponax). Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl-methylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams.

In certain embodiments, suitable pharmaceutically acceptable excipients may include essential oils of relatively low volatility, which are mostly used as aroma components, are also suitable as perfume oils, e.g. sage oil, chamomile oil, oil of cloves, melissa oil, mint oil, cinnamon leaf oil, linden blossom oil, juniper berry oil, vetiver oil, olibanum oil, *galbanum* oil, labolanum oil and lavandin oil. Other suitable oils include bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

In certain embodiments, suitable pharmaceutically acceptable excipients may include preservatives. The term "preservative", as used herein, refers to an agent that extends the storage life of the dosage form by retarding or preventing deterioration of flavor, odor, color, texture, appearance, therapeutic value, or safety. A preservative need not provide a lethal, irreversible action resulting in partial or complete microbial cell destruction or incapacitation. Sterilants, sanitizers, disinfectants, sporicides, viracides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act). Suitable preservatives include, without limitations, phenoxyethanol, a solution of paraben, pentanediol and sorbic acid, as well as silver complexes.

In certain embodiments, suitable pharmaceutically acceptable excipients may include coloring agents, such as, without limitations, colors such as e.g., white, black, yellow, blue, green, pink, red, orange, violet, indigo, and brown.

In certain embodiments, suitable pharmaceutically acceptable excipients may include, without limitations, "flavor extract" obtained by extracting a part of a raw material, e.g., animal or plant material, often by using a solvent such as ethanol or water; natural essences obtained by extracting essential oils from the blossoms, fruit, roots, etc., or from the whole plants. Additional exemplary flavoring agents for the compositions described herein may include, but not be limited to, menthol, spearmint, and cinnamon, coffee beans, other flavors or fragrances such as fruit flavors (e.g., cherry, orange, grape, etc.), quaternary ammonium bases. The effect of flavors may be enhanced using flavor enhancers like tartaric acid, citric acid, vanillin, or the like.

In certain embodiments, suitable pharmaceutically acceptable excipients may include sweetening agents such as, without limitations, one or more artificial sweeteners, one or more natural sweeteners, or a combination thereof. Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), *stevia*, chloro derivatives of sucrose such as sucralose (available as Kaltame® and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); *Stevia rebaudiana* (Stevioside), natural intensive sweeteners, such as Lo Han Kuo, polyols such as sorbitol, mannitol, xylitol, erythritol, and the like.

In certain embodiments, suitable pharmaceutically acceptable excipients may include alkalizing agent(s), such as, without limitations, magnesium oxide, ammonium hydroxide, sodium hydroxide, sodium carbonate, sodium citrate, trisodium phosphate and/or disodium phosphate.

In certain embodiments, suitable pharmaceutically acceptable excipients may include lubricant(s)/release agent (s) such as, but not limited to, fatty acids and their salts, fatty alcohols, fatty esters, fatty amines, fatty amine acetates and fatty amides. Other suitable lubricants may include, but not be limited to, glyceryl behenate (Compritol™ 888), metallic stearates (e.g., magnesium, calcium and sodium stearates), stearic acid, hydrogenated vegetable oils (e.g., Sterotex™), talc, waxes such as beeswax and camauba wax, silica, fumed silica, colloidal silica, calcium stearate, long chain fatty alcohols, boric acid, sodium benzoate and sodium acetate, sodium chloride, DL-Leucine, polyethylene glycols (e.g., Carbowax™ 4000 and Carbowax™ 6000), sodium oleate, sodium benzoate, sodium acetate, sodium lauryl sulfate, sodium stearyl fumarate (Pruv™), magnesium lauryl sulfate, stearic acid, stearyl alcohol, mineral oil, paraffin, micro crystalline cellulose, glycerin, propylene glycol and combinations thereof.

In certain embodiments, suitable pharmaceutically acceptable excipients may include diluents such as, but not limited to, lactose USP, lactose USP (anhydrous), lactose USP (spray dried), starch USP, directly compressible starch, mannitol USP, sorbitol, dextrose monohydrate, microcrystalline cellulose NF, dibasic calcium phosphate dihydrate NF, sucrose-based diluents, confectioner's sugar, monobasic calcium sulfate monohydrate, calcium sulfate dihydrate NF, calcium lactate trihydrate granularNF, dextrates NF (e.g., Emdex™), dextrose (e.g., Cerelose™) inositol, hydrolyzed cereal solids such as the Maltrons™ and Mor-Rex™, amylose, powdered cellulose (e.g., Elcema™), calcium carbonate, glycine, bentonite, polyvinylpyrrolidone, and the like.

In certain embodiments, suitable pharmaceutically acceptable excipients may include oils and fats such as, but not be limited to, almond oil, argan oil, avocado oil, canola oil, cashew oil, castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, *perilla* oil, pine nut oil, pistachio oil, poppy seed oil, pumpkin seed oil, rice bran oil, safflower oil, sesame oil, shea butter, soybean oil, sunflower oil, walnut oil, and watermelon seed oil. Other oil and fats that may be in the fill of the PVA shell may include, but not be limited to, fish oil (omega-3), crill oil, animal or vegetable fats, e.g., in their hydrogenated form, mono-, di-, and tri-glycerides with C12-, C14-, C16-, C18-, C20- and C22-fatty acids.

In certain embodiments, suitable pharmaceutically acceptable excipients may include vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids, polyacrylamides, and polyacrylic acid esters, polymethacrylic acids, polymethacrylamides, and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired; and other similar polymers; inorganic fillers, such as the oxides of magnesium aluminum, silicon, titanium, etc.

In certain embodiments, suitable pharmaceutically acceptable excipients may include a hydrophobic material, including, but not limited to, digestible, long chain ($C_8$-$C_{50}$, especially $C_{12}$-$C_{40}$), substituted or unsubstituted hydrocarbons, such as natural or synthetic waxes (such as beeswax, glycowax, castor wax and camauba wax), fatty alcohols (such as lauryl, myristyl, stearyl, cetyl or preferably cetostearyl alcohol), fatty acids, including, but not limited to, mono-diglyceride of medium chain fatty acids (such as caprylic, capric, caproic, lauric, oleic, linoleic), medium chain triglycerides, fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones.

In certain embodiments, suitable pharmaceutically acceptable excipients may include polyvinyl alcohols, polyvinyl pyrrolidone, polyalkylene oxides, polyacrylic acid, cellulose, cellulose ethers, cellulose esters, cellulose amides, polyvinyl acetates, polycarboxylic acids and salts, acetic acid, caprylic acid, oleic acid, polyaminoacids or peptides, polyamides, polyacrylamide, copolymers of maleic/acrylic acids, polysaccharides including starch and gelatin, natural gums such as xanthan, and carrageenans. For example, polymers can be selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and combinations thereof, or selected from polyvinyl alcohols, polyvinyl alcohol copolymers and hydroxypropyl methyl cellulose (HPMC), methacrylic acid/methyl methacrylate, methacrylic acid/ethyl acrylate copolymers, methacrylic acid/methyl acrylate/methyl methacrylate copolymers, shellac, hydroxypropyl methylcellulose phthalate, hydroxyl propyl methyl cellulose acetate succinate, hydroxypropyl methyl cellulose trimellitate, cellulose acetate phthalates, polyvinyl acetate phthalates, PEG-35 castor oil, caprylocaproyl polyoxyl-8 glycerides, glyceryl distearate, and combinations thereof.

In certain embodiments, suitable pharmaceutically acceptable excipients may include high HLB surfactants such as, without limitations, polysorbate 80-polyoxyethylene (20) sorbitan monooleate, polyoxyl 40 hydrogenated castor oil, polyoxyl 35 castor oil, caprylocaproyl macrogol glycerides, and combinations thereof.

In certain embodiments, suitable pharmaceutically acceptable excipients may include fillers such as, without limitations, lactose, microcrystalline cellulose, and combinations thereof.

In certain embodiments, suitable pharmaceutically acceptable excipients may include natural gums (e.g., a natural plant gum). Suitable natural gums include, without limitations, guar gum, carob gum, konjac gum, xanthan gum, *sclerotium* gum, acacia gum, cellulose gum (modified or not), or a combination thereof.

In certain embodiments, suitable pharmaceutically acceptable excipients may include emulsifiers such as, without limitations, PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Polyoxyl 10 Oleyl Ether, Ceteth-10, lsosteareth-20, Ceteareth-20, Oleth-20, Steareth-20, Steareth-21, Ceteth-20, lsoceteth-20, Laureth-23, Steareth-100, Glyceryl Stearate Citrate, Glyceryl Stearate SE (self-emulsifying), stearic acid, salts of stearic acid, polyglyceryl-3-methylglycosedistearate, or a combination thereof.

Further suitable emulsifiers are phosphate esters and the salts thereof such as cetyl phosphate (Amphisol® A), diethanolamine cetyl phosphate (Amphisol®DEA), potassium cetyl phosphate (Amphisol® K), sodium cetearyl sulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Cetearyl Glucoside, Lauryl Glucoside, Decyl Glucoside, Sodium Stearoyl Glutamate, Sucrose Polystearate and Hydrated Polyisobutene. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof.

In certain embodiments, suitable pharmaceutically acceptable excipients may include chelating agents such as, without limitations, disodium ethylenediaminetetraacetic acid (EDTA), diethylenetriaminepentaacetic acid (DTPA), N-(hydroxyethyl)-ethylenediaminetriacetic acid (HEDTA), and nitrilotriacetic acid (NTA).

In certain embodiments, suitable pharmaceutically acceptable excipients may include fatty alcohols, such as, without limitations guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

In certain embodiments, suitable pharmaceutically acceptable excipients may include esters of fatty acids, such as, without limitations esters of linear $C_6$-$C_{24}$ fatty acids with linear C3-$C_{24}$ alcohols, esters of branched $C_6$-$C_{13}$carboxyl acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerization of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerization of unsaturated fatty alcohols). Additional suitable examples of ester oils are isopropyl myristate, isopropyl palmitate, isopropyl stearate, isopropyl isostearate, isopropyl oleate, n-butyl stearate, n-hexyl laurate, n-decyl oleate, isooctyl stearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

In certain embodiments, suitable pharmaceutically acceptable excipients may include other adjuvants, such as, without limitations, diethylhexyl 2,6-naphthalate, di-n-butyl adipate, di(2-ethylhexyl)-adipate, di(2-ethyl hexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups.

In certain embodiments, suitable pharmaceutically acceptable excipients may include natural or synthetic triglycerides (including glyceryl esters and derivatives), such as, without limitations, di- or triglycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borage oil, etc. Additional suitable excipients include waxes including esters of long-chain acids and alcohols as well as compounds having wax-like properties, e.g., carnauba wax, beeswax (white or yellow), lanolin wax, candelilla wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

In certain embodiments, suitable pharmaceutically acceptable excipients may include pearlescent waxes, such as, without limitations, alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially lauryl and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

In certain embodiments, suitable pharmaceutically acceptable excipients may include hydrocarbon oils, such as, without limitations, mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

In certain embodiments, suitable pharmaceutically acceptable excipients may include silicones or siloxanes (organosubstituted polysiloxane), such as, without limitations, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

In certain embodiments, suitable pharmaceutically acceptable excipients may include emulsifiers, such as, without limitations, carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethylene glycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycol ether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, $C_8$-$C_{22}$ alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropyene sulfonate, sodium lauryl sulfates, ammonium and ethanolamine lauryl sulfates, lauryl ether sulfates, sodium laureth sulfates, sulfosuccinates, acetyl isothionates, alkanolamide sulfates, taurines, methyl taurines, imidazole sulfates. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene). Zwitterionic surfactants that carry at least one quatemary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkyl betaine, N-alkylaminobetaines. Alkylimidazolines, alkylopeptides, lipoaminoacides, self-emulsifying bases and the compounds as described in K. F. DePolo, A short textbook of cosmetology, Chapter 8, Table 8-7, p 250-251.

Suitable nonionic bases include, without limitations, PEG-6 beeswax (and) PEG-6 stearate (and) polyglyceryl-2-isostearate, glyceryl stearate (and) PEG-100 stearate, PEG-5 glyceryl stearate, sorbitan oleate (and) polyglyceryl-3 ricinoleate, sorbitan stearate and sucrose cocoate, glyceryl stearate and laureth-23, cetearyl alcohol and ceteth-20, cetearyl alcohol and polysorbate 60 and PEG-150 and stearate-20, cetearyl alcohol and cetearyl polyglucoside, cetearyl alcohol and ceteareth-20, cetearyl alcohol and PEG-40 castor oil, cetearyl alcohol and PEG-40 castor oil and sodium cetearyl sulfate, stearyl alcohol and steareth-7 and steareth-10, cetearyl alcohol and szeareth-7 and steareth-10, glyceryl stearate and PEG-75 stearate, propylene glycol ceteth-3 acetate, propylene glycol isoceth-3 acetate, cetearyl alcohol and ceteth-12 and oleth-12, PEG-6 stearate and PEG-32 stearate, PEG-6 stearate and ceteth-20 and steareth-20, PEG-6 stearate and ceteth-20 and glyceryl stearate and steareth-20, glyceryl stearate and ceteareth-20.

Suitable anionic alkaline bases includes, without limitations, PEG-2 stearate SE, glyceryl stearate SE, propylene glycol stearate. Anionic acid bases such as cetearyl Alcohol and Sodium cetearyl sulfate, cetearyl alcohol and sodium lauryl sulfate, trilaneth-4 phosphate and glycol stearate and PEG-2 stearate, glyceryl stearate and sodium lauryl Sulfate. Cationic acid bases such as cetearyl alcohol and cetrimonium bromide.

In certain embodiments, suitable pharmaceutically acceptable excipients may include adjuvants and additives, such as, without limitations, surfactants, super-fatting agents, consistency regulators, thickeners, polymers, stabilizers, biogenic active ingredients, swelling agents, further UV light-protective factors, antioxidants, hydrotropic agents, preservatives, self-tanning agents, solubilizers, perfume oils, colorants, bacteria-inhibiting agents and the like.

In certain embodiments, suitable pharmaceutically acceptable excipients may include super-fatting agents, such as, without limitations, lanolin and lecithin and also polyethoxylated or acetylated lanolin and lecithin derivatives, polyol fatty acid esters, monoglycerides and fatty acid alkanolamides, the latter simultaneously acting as foam stabilizers.

In certain embodiments, suitable pharmaceutically acceptable excipients may include surfactants, such as, without limitations, fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, .alpha.-olefin sulfonates, ethercarboxylic acids, alkyl oligoglucosides, fatty acid glucamides, alkylamidobetaines and/or protein fatty acid condensation products, the latter preferably being based on wheat proteins.

In certain embodiments, suitable pharmaceutically acceptable excipients may include consistency regulators/thickeners and rheology modifiers, such as, without limitations, silicium dioxide, magnesium silicates, aluminium silicates, polysaccharides or derivatives thereof for example hyaluronic acid, xanthan gum, guar-guar, agar-agar, alginates, carrageenan, gellan, pectines, or modified cellulose such as hydroxycellulose, hydroxypropylmethylcellulose. In addition polyacrylates or homopolymer of reticulated acrylic acids and polyacrylamides, carbomer (CARBOPOL types 980, 981, 1382, ETD 2001, ETD2020, ULTREZ 10) or SALCARE range such as SALCARE SC80 (steareth-10 allyl ether/acrylates copolymer), Salcare SC81 (acrylates copolymer), Salcare SC91 and Salcare AST (sodium acrylates copolymer/PPG-1 trideceth-6), SEPIGEL 305 (polyacrylamide/laureth-7), SIMULGEL NS and SIMULGEL EG (hydroxyethyl acrylate/sodium acryloyldimethyl taurate copolymer), STABILEN 30 (acrylates/vinyl isodecanoate crosspolymer), PEMULEN TR-1 (acrylates/C10-30 alkyl acrylate crosspolymer), LUVIGEL EM (sodium acrylates copolymer), ACULYN 28 (acrylates/beheneth-25 methacrylate copolymer), etc.

In certain embodiments, suitable pharmaceutically acceptable excipients may include polymers, such as, without limitations, an anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylate-tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatized cellulose ethers and silicones. Furthermore, the polymers as described in EP 1093796 (pages 3-8, paragraphs 17-68) may be used.

In certain embodiments, suitable pharmaceutically acceptable excipients may include antioxidants, such as, without limitations amino acids (e.g. glycine, histidine, tyrosine, tryptophan) and derivatives thereof, imidazoles (e.g. urocanic acid) and derivatives thereof, peptides, such as D,L-camosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, camosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

In certain embodiments, suitable pharmaceutically acceptable excipients may include hydrotropic agents, such as, without limitations, ethoxylated or non-ethoxylated mono-alcohols, diols or polyols with a low number of carbon atoms or their ethers (e.g. ethanol, isopropanol, 1,2-dipropanediol, propylene glycol, glycerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

In certain embodiments, suitable pharmaceutically acceptable excipients may include preservatives, such as, without limitations, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichlorobenzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo-A short textbook of cosmetology, Chapter 7, Table 7-2, 7-3, 7-4 and 7-5, p 210-219.

In certain embodiments, suitable pharmaceutically acceptable excipients may include bacteria-inhibiting agents, such as, without limitations, 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent.

Other pharmaceutically acceptable excipients may also be utilized as recognized by those skilled in the art.

In certain embodiments, pharmaceutically acceptable excipients may be included (individually or cumulatively) in the pharmaceutical compositions described herein in a concentration ranging from any of about 5 wt %, about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, about 90 wt %, about 95 wt %, or about 99 wt %, or any sub-range or single value therein based on the total weight of the composition.

Method of Preparation

In certain embodiments, the instant disclosure is directed to a method of preparing any of the compositions described herein. In certain embodiments, the method includes combining a therapeutically effective amount of a BK channel modulating compound with one or more pharmaceutically acceptable excipients.

The various compositions described herein may be formulated to have a customized release profile for the active agent, such as, without limitations, an immediate release profile, a controlled release profile, a delayed release profile, an enteric release profile, a zero order release profile, a first order release profile, a pulsatile release profile, a targeted release in a certain location within the body (such as a target location within the gastrointestinal tract), and the like.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A method of treating a disease or condition modulated by large-conductance potassium channels comprising administering, to a patient in need thereof, an effective amount of a large-conductance potassium channel modulating compound selected from compound(s) of Formula (I):

(I)

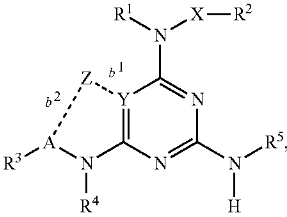

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, $—NR^1R^2$, $—C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, $—OR^1$, $—NR^1R^2$, $—C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond blis nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH;

or, (ii) Z is CH, bond $b^2$ is a double bond, and A is C;

or a salt thereof; wherein the disease or condition is a neurological disorder selected from epilepsy, paroxysmal dyskinesia, or schizophrenia.

2. The method of claim 1, wherein the compound is an agonist.

3. The method of claim 1, wherein the compound is an antagonist.

4. The method of claim 1, wherein the compound modulates at one or both of the pore gate or the voltage sensing domain of the large-conductance potassium channel.

5. The method of claim 1, wherein the compound modulates at one or both of the RCK1 or the RCK2 of the large-conductance potassium channel.

6. The method of claim 1, wherein the large-conductance potassium channel is located at one or both of a pre-synaptic or post-synaptic site.

7. The method of claim 1, wherein the administration route is selected from oral, intravenous, nasal, inhalational, topical, buccal, rectal, pleural, peritoneal, vaginal, intramuscular, subcutaneous, transdermal, epidural, intratrachael, otic, intraocular, or intrathecal route.

8. A method of treating a disease or condition modulated by large-conductance potassium channels comprising administering, to a patient in need thereof, an effective amount of a large-conductance potassium channel modulating compound selected from compound(s) of Formula (I):

(I)

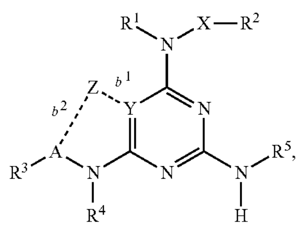

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, $—NR^1R^2$, $—C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, $—OR^1$, $—NR^1R^2$, $—C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH;

or, (ii) Z is CH, bond $b^2$ is a double bond, and A is C;

or a salt thereof; wherein the disease or condition is a cardiac disorder selected from cardiac ischemia or cardiac hypoxia.

9. The method of claim 8, wherein the compound is an agonist.

10. The method of claim 8, wherein the compound is an antagonist.

11. The method of claim 8, wherein the compound modulates at one or both of the pore gate or the voltage sensing domain of the large-conductance potassium channel.

12. The method of claim 8, wherein the compound modulates at one or both of the RCK1 or the RCK2 of the large-conductance potassium channel.

13. The method of claim 8, wherein the large-conductance potassium channel is located at one or both of a pre-synaptic or post-synaptic site.

14. The method of claim 8, wherein the administration route is selected from oral, intravenous, nasal, inhalational, topical, buccal, rectal, pleural, peritoneal, vaginal, intramuscular, subcutaneous, transdermal, epidural, intratrachael, otic, intraocular, or intrathecal route.

15. A method of treating a disease or condition modulated by large-conductance potassium channels comprising administering, to a patient in need thereof, an effective amount of a large-conductance potassium channel modulating compound selected from compound(s) of Formula (I):

(I)

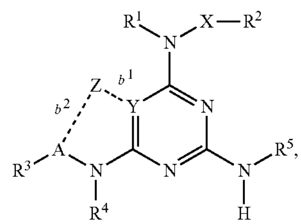

wherein:

$R^1$ and $R^2$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, alkynyl, substituted alkynyl, cycloalkyl, substituted cycloalkyl, alkenyl, substituted alkenyl, $—NR^1R^2$, $—C(O)OR^1$, acyl, or aryl;

$R^4$ is H, alkyl, or substituted alkyl;

$R^5$ is H, alkyl, propargylic, substituted propargylic, homopropargylic, substituted homopropargylic, substituted alkyl, cycloalkyl, substituted cycloalkyl, alkenyl, substituted alkenyl, $—OR^1$, $—NR^1R^2$, $—C(O)OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and: (i) Z is H, bond $b^2$ is a single bond, and A is CH; or, (ii) Z is nil, bond $b^2$ is nil, and A is a single bond; and, if Y is C, then bond $b^1$ is a single bond, and: (i) Z is $CH_2$, bond $b^2$ is a single bond, and A is CH;

or, (ii) Z is CH, bond $b^2$ is a double bond, and A is C;

or a salt thereof; wherein the disease or condition is a cerebral disorder selected from cerebral ischemia or cerebral hypoxia.

16. The method of claim 15, wherein the compound is an agonist.

17. The method of claim 15, wherein the compound is an antagonist.

18. The method of claim 15, wherein the compound modulates at one or both of the pore gate or the voltage sensing domain of the large-conductance potassium channel.

19. The method of claim 15, wherein the compound modulates at one or both of the RCK1 or the RCK2 of the large-conductance potassium channel.

20. The method of claim 15, wherein the large-conductance potassium channel is located at one or both of a pre-synaptic or post-synaptic site.

21. The method of claim 15, wherein the administration route is selected from oral, intravenous, nasal, inhalational, topical, buccal, rectal, pleural, peritoneal, vaginal, intramuscular, subcutaneous, transdermal, epidural, intratrachael, otic, intraocular, or intrathecal route.

* * * * *